United States Patent [19]

Evangelista et al.

[11] Patent Number: 5,262,299

[45] Date of Patent: Nov. 16, 1993

[54] ENZYME-AMPLIFIED LANTHANIDE CHELATE LUMINESCENCE

[75] Inventors: Ramon A. Evangelista, Scarborough; Eva F. G. Templeton, Willowdale; Alfred Pollak, Toronto, all of Canada

[73] Assignee: Kronem Systems, Inc., Ontario, Canada

[21] Appl. No.: 612,171

[22] Filed: Nov. 13, 1990

[30] Foreign Application Priority Data

Dec. 4, 1989 [GB] United Kingdom ............... 8927503

[51] Int. Cl.[5] ............................................ C12G 1/68
[52] U.S. Cl. ................................. 435/6; 435/21; 435/25; 435/28; 435/968; 435/7.4; 435/7.91; 436/56; 436/501; 436/512; 436/546; 436/800; 536/23.1; 935/76; 935/77; 935/98; 935/81
[58] Field of Search ................... 435/6, 968, 21, 25, 435/28, 7.4, 7.91; 536/27, 23.1; 935/78, 77, 76, 81; 436/56, 501, 800, 512, 546

[56] References Cited

U.S. PATENT DOCUMENTS

| | | | |
|---|---|---|---|
| 4,058,732 | 11/1977 | Wieder | 424/7 |
| 4,110,442 | 8/1978 | Barra et al. | 424/212 |
| 4,259,313 | 3/1981 | Frank et al. | 424/8 |
| 4,374,120 | 2/1983 | Soini et al. | 436/546 |
| 4,585,790 | 1/1986 | Hemmila | 436/537 |
| 4,587,223 | 5/1986 | Soini et al. | 436/536 |
| 4,637,988 | 1/1987 | Hinshaw et al. | 436/546 |
| 4,772,563 | 9/1988 | Evangelista et al. | 436/518 |
| 4,808,541 | 2/1989 | Mikola et al. | 436/501 |
| 4,837,169 | 6/1989 | Toner | 436/546 |

FOREIGN PATENT DOCUMENTS

| | | |
|---|---|---|
| 0131830 | 7/1984 | European Pat. Off. . |
| 0138357 | 8/1984 | European Pat. Off. . |
| 0146039 | 11/1984 | European Pat. Off. . |
| 0146815 | 11/1984 | European Pat. Off. . |
| 0192168 | 2/1986 | European Pat. Off. . |
| 0195413 | 3/1986 | European Pat. Off. . |
| 0203047 | 5/1986 | European Pat. Off. . |
| 0324323 | 9/1988 | European Pat. Off. . |
| 84/04970 | 6/1984 | PCT Int'l Appl. . |
| 87/03622 | 12/1986 | PCT Int'l Appl. . |
| 88/02784 | 10/1987 | PCT Int'l Appl. . |
| 89/04375 | 10/1988 | PCT Int'l Appl. . |
| 89/10975 | 4/1989 | PCT Int'l Appl. . |

OTHER PUBLICATIONS

R. H. Bromilow et al., "Intramolecular general acid catalysis of phosphate monoester hydrolysis, hydrolysis of 2-Carboxyphenyl dihydrogen phosphate," *Chemical Abstracts*, vol. 76, 1972, p. 312.

5-Chlor-Salicylsaure, Beilstein, Syst. No. 1066, p. 103.

I. Hemmilä, Lanthanides as probes for time-resolved fluorometric immunoassays, Scad J Clin Lab Invest 1988; 48: 389-400.

Robert C. Morton, Streptavidin-Based Macromolecular Complex Labeled with a Europium Chelator Suitable for Time-Resolved Fluorescence Immunoassay Applications, Analytical Chemistry, vol. 62, No. 17, Sep. 1, 1990, pp. 1841-1845.

Eleftherios P. Diamandis, Time-resolved fluoroescence using a europium chelate of 4,7-bis(chlorosulfophenyl-)-1,10-phenanthroline-2,9-dicarboxylic acid (List continued on next page.)

*Primary Examiner*—Amelia Burgess Yarbrough
*Attorney, Agent, or Firm*—Bell, Seltzer, Park & Gibson

[57] ABSTRACT

A method and compounds useful for this method are described for enzyme-amplified signal detection in analytical assays requiring extremely high detection sensitivity which uses a substrate capable of being transformed by an enzyme from a compound which does not form a luminescent lanthanide chelate into a product which forms a luminescent lanthanide chelate. The method in which a substrate not capable of forming a highly luminescent lanthanide chelate is enzymatically altered to produce a product which forms a highly luminescent lanthanide chelate and hence is particularly useful in time-resolved luminescence analysis as required in many different heterogeneous or homogeneous assay formats is described herein.

22 Claims, 10 Drawing Sheets

OTHER PUBLICATIONS (BCPDA), Journal of Immunological Methods, 112 (1988) pp. 43–52.

C. J. Stanley, Enzyme amplitication; A New Technique For Enhancing The Speed And Sensitivity Of Enzyme Immunoassays, American Biotechnology Laboratory, May./Jun. 1985.

G. J. R. Barnard, The Development of Luminescence Immunoassays, Med. Lab. Sci. (1987) 44, pp. 249–266.

Axel Johannsson, Enzyme amplification for immunoassays; Detection limit of one hundredth of an attomole, Journal of Immunological Methods, 87 (1986), pp. 7–11.

Eleftherios P. Diamandis, Immunoassays with Time-Resolved Fluoroescence Spectroscopy; Principles and Applications, Clinical Biochemistry, vol. 21, Jun. 1988, pp. 139–150.

Michael Oellerich, Principles of Enzyme-immunoassays, Methods of Enzymatic Analysis, Third Edition, vol. I Fundamentals 1983, pp. 233–260.

G. G. Guilbault, Principles of luminescence spectroscopy. Luminescent determination of clinically and agriculturally important samples, Pure and Appl. Chem., vol. 57, No. 3, pp. 495–514, 1985.

Jayne A. Matthews, Analytical Strategies for the Use of DNA Probes, Analytical Biochemistry 169, 1–25 (1988).

4                               0

1 2 3 4 5 6

ENZYME-AMPLIFIED LANTHANIDE CHELATE LUMINESCENCE

FIELD OF THE INVENTION

This invention relates to a method for enzymatically amplifying signal detection in analytical assays, more particularly, in assays requiring extremely high detection sensitivity. This invention also relates to novel compounds used in this method. The types of assay which can utilize this detection system include nucleic acid hybridization assays, and immunoassays in which an enzyme is utilized as a labelling group and direct assays for specific enzyme activity.

BACKGROUND OF THE INVENTION

Bioanalytical assays such as nucleic acid hybridization assays and immunoassays are extremely important in a variety of fields, for example diagnostic medicine, forensics, genetics, and drug and agricultural testing. The use of enzymes as labelling groups in such assays is prevalent due to the intrinsic amplification provided by the activity of the enzyme in producing a large number of detectable product molecules per molecule of enzyme. In addition, assays of biological samples for specific enzymatic activity are widely used in diagnostic medicine as well as in biological and medical research fields. It is always desirable to improve the sensitivity of such assays. One way to do so is to improve the detectability of the product molecule, and hence the detectability of the enzyme itself, whether the enzyme is the analyte or is used as a labelling group.

Currently such assays are typically performed using colorimetric, chemiluminescence or fluorescence detection, in which a colorless or nonluminescent substrate is converted into a colored, chemiluminescent or fluorescent product, respectively, by the action of the enzyme. The product of the enzymatic reaction can be measured in solution, or alternately can be measured after deposition onto a solid phase such as a membrane or polystyrene support. Colorimetric assays are generally the least sensitive due to the poor sensitivity intrinsic to measurement of light absorption, which results in poor detectability of the product. The measurement of light emission is intrinsically a more sensitive technique and the theoretical detectability of chemiluminescent or fluorescent products is better. Chemiluminescent detection is in fact quite sensitive but is limited to the use or detection of a few specific enzymes due to the limited number of reactions currently known which form chemiluminescent products. Fluorescence detection can be used with a much wider variety of enzymes, but conventional fluorescence detection suffers from difficulty in discriminating specific fluorescence signal from nonspecific background signals, which restrict the practical detection limit of an assay. A number of such methods and their use in immunoassays and nucleic acid hybridization assays are reviewed in the following references: GJR Barnard & WP Collins, Med. Lab. Sci. (1987) 44 249-66; A Johannson, DH Ellis, DL Bates, AM Plumb, CJ Stanley, J. Immunol. Meth. (1986) 87 7-11; EP Diamandis, Clin. Biochem. (1988) 87 139-50; M Oellerich, Meth. Enzym. Anal. Vol. I 1983 233-60; CG Guilbault, Pure Appl. Chem. (1985) 57 495-514; and JA Matthews & LJ Kricka Anal. Biochem. (1988) 169 1-25.

Time-resolved luminescence detection of lanthanide chelates has been utilized in order to decrease nonspecific background signals. Background signals from other light emission or scattering processes (resulting from scattering of the excitation light) can be reduced by taking advantage of the unusual luminescence characteristics of lanthanide chelates, particularly of europium and terbium. Such chelates can exhibit strongly red-shifted, narrow-band, long-lived emission after excitation of the chelate at substantially shorter wavelengths. Typically, the chelate possesses a strong ultraviolet absorption band due to a chromophore which is part of the chelating molecule and located close to the lanthanide in the chelate. Subsequent to light absorption by the chromophore, if the energy levels of the chromophore and lanthanide are suitably matched, the excitation energy can be transferred from the excited chromophore to the lanthanide. This is followed by luminescence emission characteristic of the lanthanide. The use of pulsed excitation and time-gated detection combined with narrow-band emission filters allows for specific detection of the luminescence from the lanthanide chelate only, rejecting emission from other species present in the sample which are typically shorter-lived or have shorter wavelength emission. In currently existing assay formats using this principle, a lanthanide chelating agent is utilized as the labelling group. In some cases the chelating agent itself forms a luminescent lanthanide chelate which is measured directly and is usually bound by some method to a solid support. Such methods are outlined in the following patents: U.S. Pat. No. 4,374,120 (Soini & Hemmila), U.S. Pat. No. 4,637,988 (Hinshaw et al.), EP 0 203 047 (Kankare & Takalo), U.S. Pat. No. 4,259,313 (Frank & Sundberg), U.S. Pat. No. 4,058,732 (Wieder), and U.S. Pat. No. 4,772,563 (Evangelista & Pollak). In other cases the lanthanide must be released into solution to be measured in the presence of luminescence enhancing reagents, usually consisting of a combination of a detergent and a weakly complexing energy transfer reagent as illustrated in patents U.S. Pat. No. 4,565,790 (Hemmila & Dakubu) and WO 89/04375 (Musso et al.). Luminescence detection of certain lanthanide chelates has also been disclosed in EP 0 195 413 (Hale & Solas).

SUMMARY OF THE INVENTION

In a method for detecting luminescence emitted from an excited lanthanide metal chelate associated with an analyte, an aspect of the invention provides the step of:

i) enzymatically converting a selected substrate by use of an enzyme into a chelator which in the presence of a lanthanide metal ion forms a luminescent lanthanide metal chelate. The selection of the substrate is determined by the substrate in unconverted form being noncompetitive with the lanthanide metal chelate when exposed to radiation which causes the chelate to luminesce.

According to another aspect of the invention, the substrate of the above method is selected from the group represented by the formula:

FORMULA I wherein $Z_1$ is a UV-absorbing aromatic chromophoric group containing one or more heteroatoms of oxygen, nitrogen or sulfur;

A is at least one ineffective coordinating group which is enzymatically hydrolyzable or enzymatically oxidizable to an effective coordinating group for said chelator or to a group which alters the excited state energy of chromophore $Z_1$ resulting thereby in increased luminescence of said chelated lanthanide metal ion;

$W_1$ is hydrogen or a group for increasing chelation by said chelator of said lanthanide metal ion where subsequent to said enzymatic conversion $W_1$ reduces number of coordinating sites available for water molecules; and $R_1$ is hydrogen or at least one group which is hydrophobic to limit thereby diffusion in an aqueous medium of said chelator or a group which alters the excited state energy of chromaphore $Z_1$ resulting thereby in increased luminescence of said chelated lanthanide metal ion.

According to another aspect of the invention, novel substrates are selected from the group represented by the formula:

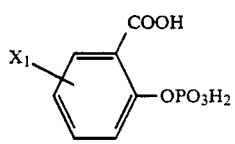

FORMULA II wherein $X_1$ is hydrogen, halogen, $C_2$ to $C_{20}$ alkyl, $C_2$ to $C_{20}$ aryl, $C_2$ to $C_{20}$ aryl containing at least one heteroatom, a heteroaromatic group of pyridine, furan, pyrrole and thiophene which are ring unsubstituted or ring substituted with $C_1$ to $C_{10}$ alkyl, or halogen, trityl, 2,4-difluorophenyl; and wherein $X_1$ is a substituent at one of the 3, 4, 5, or 6 carbon atom positions on the benzene ring.

According to another aspect of the invention, a kit for use in the method of detecting luminescence emitted from an excited lanthanide metal chelate associated with an analyte comprises:

a. a selected substrate of Formula I;
b. a lanthanide metal ion; and
c. one or more reaction vessels.

DEFINITIONS

The following definitions facilitate understanding of the acronyms used in the description of the invention.

AP:
Alkaline phosphatase
ASA:
Acetylsalicylic acid
BCAHAP: 2-[N,N-bis(carboxymethyl)amino]-acetophenone-4'-phosphate
BCAHA:
2-[N,N-bis(carboxymethyl)amino]-4'-hydroxyacetophenone
BSA:
Bovine Serum Albumin
DBDA:
4,5 - dihydroxy - 1,3 - benzenedisulfonic acid
DEASAP:
4 - diethylaminosalicyl phosphate
EALL:
Enzyme Amplified Lanthanide Luminescence
EDTA:
ethylenediaminetetraacetate or ethylenediaminetetraacetic acid
Eu:
Europium (III)
FSA:
5-fluorosalicylic acid
FSAP:
5-fluorosalicyl phosphate
GOD:
Glucose oxidase
HBCAB:
4-hydroxy-3,5-bis[N,N-bis(carboxymethyl)aminomethyl]benzophenone
HBCABP:
3,5-bis[N,N-bis(carboxymethyl)aminomethyl]benzophenone-4-phosphate
HBCAB.dee:
4-hydroxy-3-[N,N-bis(carboxymethyl)aminomethyl]-benzophenone diethyl ester
HBCAB.tee:
4-hydroxy-3,5-bis[N,N-bis(carboxymethyl)aminomethyl]benzophenone tetraethyl ester
HRP:
Horseradish peroxidase
Mg:
Magnesium (II)
MSAP:
5 - methylsalicyl phosphate
NDSAP:
5-n=dodecylsalicyl phosphate
PDA:
1,10-Phenanthroline-2,9-dicarboxylic acid
PDAdh:
1,10-phenanthroline-2,9-dicarboxylic acid dihydrazide
PLE:
pig liver esterase
SA:
salicylic acid
SAld:
salicylaldehyde
SAP:
salicyl phosphate
Tb:
terbium (III)
TOSA:
5-tert-octyl salicylic acid
TOSAP:
5-tert-octyl salicyl phosphate
TRIS:
tris(hydroxymethyl)aminomethane
TRSAP:
5-tritylsalicyl phosphate

BRIEF DESCRIPTION OF THE DRAWINGS

Preferred embodiments of the invention shall be discussed with reference to the accompanying drawings wherein.

DETAILED DESCRIPTION OF THE PREFERRED EMBODIMENTS

Figure 1:
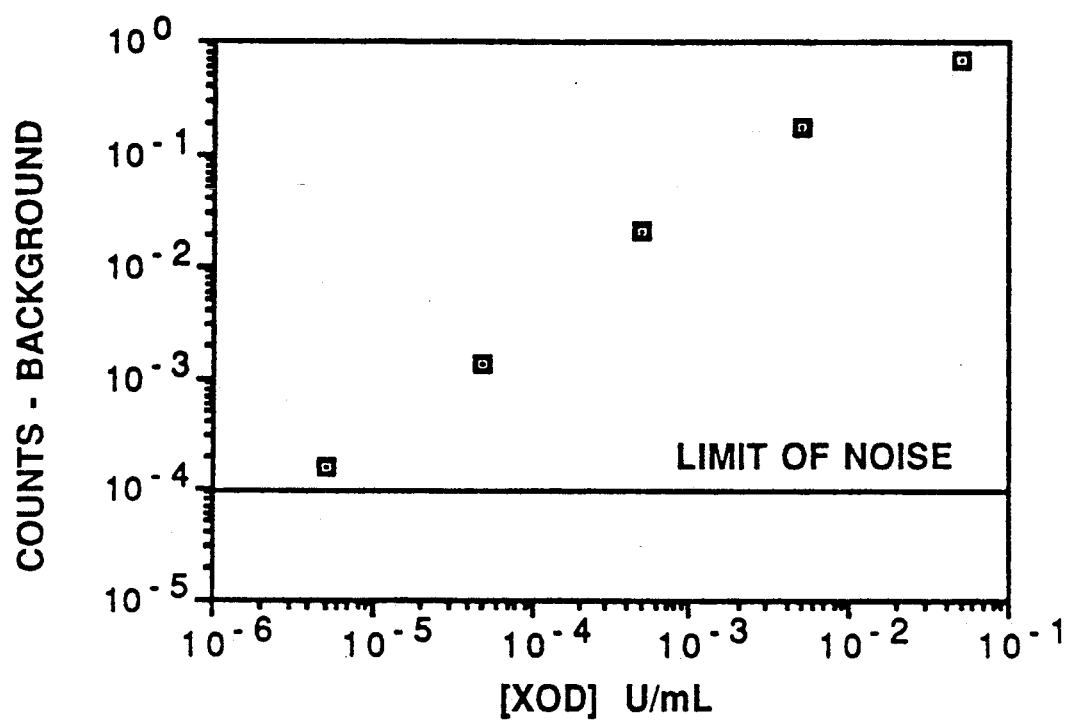
FIG. 1 illustrates the determination of xanthine oxidase using salicylaldehyde as substrate, as observed by measurement of the luminescence of Tb:salicylic acid (SA):EDTA complex from the SA produced by the enzymatic reaction.

In the present invention high detection sensitivity signal generation is achieved in a method for enzymatically amplifying signal detection through utilization of a selected substrate which is capable of being transformed by an enzyme from a compound which does not form a luminescent lanthanide chelate into a chelator which forms a luminescent lanthanide chelate with a lanthanide metal ion. This may occur in the presence or absence of a co-chelator. The substrate selected in unconverted form is non-competitive with the lanthanide metal chelate when exposed to radiation which causes the lanthanide metal chelate to luminesce. For example, the selected substrate may have a degree of luminescence in the presence of the lanthanide metal. It is understood, however, that such luminescence from the substrate does not interfere with the luminescence signal from the lanthanide metal ion chelate. This may be due to the luminescent emission from the substrate occurring at a different time than the emissions from the lanthanide metal chelate or may also be due to the emission from the substrate being considerably weaker than the emission occurring at the same time from the chelate or the substrate may be excited at a wavelength which is substantially different from that of the chelate. Any luminescence from the substrate, should it exist or not exist, results in a selected substrate which is hence non-competitive during the luminescent detection step with the lanthanide metal chelate.

The luminescent lanthanide chelate thus formed is detected using either normal or time-resolved luminescence methods. This detection system can be utilized in many different heterogeneous assay formats, including microtitration plate formats for immunoassays and dot blot or Southern blot formats for hybridization assays. In addition, it may be utilized for a variety of homogeneous, heterogeneous or in situ assay formats and for specific enzyme activity.

In accordance with an aspect of the present invention a new method is provided for detection and/or quantification of an enzyme, where the enzyme is either used as a labelling group (for example bound to a hapten, antibody, binding protein, plant lectin, carbohydrate, hormone, or nucleic acid), or is itself the analyte of interest. In this method a substrate is enzymatically converted from a compound which under the conditions of the luminescence measurement does not form a highly luminescent chelate with a lanthanide ion to a product (chelator) which does form such a lanthanide chelate.

The necessary alteration in the luminescent properties of the product, resulting in a substantially increased yield of luminescent lanthanide complex formation on conversion from the substrate, may be due to any combination of one or more of the following factors: more efficient net energy transfer from the product to the lanthanide ion in the chelate; more efficient light absorption by the product lanthanide chelate than for the substrate lanthanide chelate due to an alteration of spectroscopic properties energy levels; or, an increase in the number of groups coordinated to the lanthanide in the product compared to the substrate as a result of enzymatic action, for example due to addition of new coordinating groups, coupling of two species each containing coordinating groups, alteration of existing poorly coordinating groups to strongly coordinating groups, or removal of blocking groups in the vicinity of the chelating site which may hinder complex formation, any of which can result in a higher binding constant for the formation of complexes of the product with the lanthanide, and a higher yield of luminescence due to exclusion from the coordination sphere of the lanthanide of water molecules which are known to quench the luminescence of some lanthanides. The complexes formed between the product and the lanthanide may be of any stoichiometry; in particular complexes of the type in lanthanide:product (n=1 to 3) are preferred. In addition, the complex may contain other coordinating species present in the solution, such as buffer ions or ethylenediaminetetraacetate (EDTA) ion, which are known to enhance the luminescence of the product:lanthanide chelate due to exclusion of water from the coordinating sites of the lanthanide. Thus, in this invention, the principles of enzymatic amplification and time-resolved luminescence of lanthanide chelates are combined in order to give the higher sensitivity provided by the utilization of both signal amplification and background rejection.

In addition, the method of the present invention can be applied to detection of a wider variety of enzymes than are currently used for other forms of detection, due to the large number of possible enzymatic reactions resulting in a significant alteration of the chelating or spectroscopic properties of the substrate: this imparts the advantage of improved background rejection compared to normal fluorophores, allowing improved detection limits for the enzyme. This is based on the specific luminescence properties of the lanthanide chelates which permit practical and inexpensive wavelength filtering and time-gating to be performed during the measurement in order to detect only the luminescence of the lanthanide chelate. The present invention differs from previous methods which are used for the signal detection in bioanalytical assays using the principle of time-resolved luminescence of lanthanide chelates (see the aforementioned Wieder, Musso et al., Hinshaw et al., Frank & Sundberg, Evangelista & Pollak, Kankare & Takalo, Hale & Solas), in that in the present invention, the chelating agent is not directly attached as a labelling group. The present invention is differentiated further from other luminescence methods for the detection or quantitation of specific enzymes where the enzyme is the analyte, in that the luminescence of the enzymatic product itself is not measured, rather the luminescence of the complex formed between the product and a lanthanide ion is quantitated. Examples of suitable lanthanides include, but are not limited to, terbium, europium, samarium and dysprosium. The amplification by the enzyme coupled with the lanthanide-chelate luminescence imparts the advantage of improved background rejection as compared to normal fluorophores thereby permitting improved detection limits for the enzyme. It is recognized in the present invention that it is the specific luminescence properties of the lanthanide chelates which permit practical and inexpensive wavelength filtering and time-gating to be performed during the measurement in order to detect only the luminescence of the lanthanide chelate.

Another aspect of the present invention lies in the use of an enzyme as a label, or analyte, which reacts with the selected substrate to produce a non-chelator product which can subsequently react with a compound not capable of forming a luminescent lanthanide chelate, in order to form a second product chelating agent capable of forming such a chelate. One example of such a product is an oxidizing agent such as hydrogen peroxide. This principle has been illustrated using detection methods other than time-resolved luminescence (CJ Stanley, F Paris, A Plumb, A Webb, A Johannson, Am. Biotech. Lab. (1985) May/June).

In addition, the invention can be utilized for assay formats in which the labelling group is a first enzyme which produces a cofactor or substrate used by a second enzyme present in solution to subsequently produce the desired product capable of luminescent lanthanide chelate formation, or for a format in which a first enzyme produces an inhibitor for a such a second enzyme, causing a reduction in measured signal when the first enzyme is present. The method is suitable for use in any assay format in which quantitation of the amount of enzyme present is appropriate. This includes many types of separation immunoassays or hybridization assays wherein the enzyme is used as a label on a hapten, protein or nucleic acid fragment, as examples, which when bound to its specific antibody, hapten or complementary nucleic acid sequence can be separated from unbound species. The enzyme may be directly or indirectly, covalently or noncovalently bound, and present as a single or multiple label. Such formats include the enzyme-linked immunosorbent assay, dot-blot, Southern blot or sandwich hybridization assays, in situ hybridization or immunoassays, and gel permeation separation assays. The luminescent product may be detected in solution, deposited onto a solid support, or suspended in an inhomogeneous matrix such as an electrophoretic gel.

Examples of known assay methodologies and reagents used in these assays are detailed in the following patents: Ep 0 192 168 (Dattagupta), EP 0 146 815 (Albarella & Anderson), EP 0 146 039 (Albarella et al.), WO 84/04970 (Ward et al.), WO 87/03622 (Schneider & Shank), EP 0 138 357 (Landes), and EP 0 131 830 (Dattagupta). All of these methodologies may be adapted by the EALL method of the present invention.

In addition, the method is suitable for use in assays for specific enzymes, with the choice of a suitable substrate, in order to establish the presence, specificity or specific activity of a particular enzyme in a sample, for example, in tissue, either homogenized or in section, in cell cultures, or immobilized on a solid support. The enzyme whose activity or concentration is to be determined may be present in other biological tissue samples such as whole blood, plasma or serum. Alternatively, the enzyme may be directly or indirectly conjugated to antibody which is part of the immunological complex in an immunoassay, present as an enzyme which is directly or indirectly conjugated to a nucleic acid probe which is part of a DNA-DNA or DNA-RNA duplex in a nucleic acid hybridization assay, or, by suitable means, the enzyme is immobilized on to a solid support. As such, the invention, is equally applicable to DNA sequencing techniques as well as DNA probes.

The enzymatic reaction step of the present invention need not be performed under the same reaction conditions as the conditions for the formation of the lanthanide chelate and measurement of the luminescence. The lanthanide, and any co-chelating agents, such as EDTA, may be present during the enzymatic reaction or may be added subsequently. The pH of the solution may also be altered to improve complex formation. The luminescence of the product chelate is measured under conditions intended to optimize discrimination against any small background signals. The measurement of the luminescence may be performed under conditions of continuous illumination with ultraviolet light, with an excitation wavelength filter chosen to excite preferentially the product/lanthanide chelate over the substrate if possible, and an emission wavelength filter chosen to select for the lanthanide emission. Preferably, the measurement is performed using, in addition to the aforementioned wavelength filtering, pulsed ultraviolet excitation and time-gated detection optimized with respect to the luminescence lifetime of the chelate; this method of measurement provides the best discrimination against nonspecific background luminescence signals.

A number of enzyme-protein and enzyme-nucleic acid conjugates are commercially available or have been reported in the literature and can be used by a person skilled in the art with the method and reagents of the present invention.

In view of the breadth of luminescent-type assays to which this invention may be applied, there is a broad range of reference material describing processes for making various types of enzyme conjugates which are, in turn, useful in this invention. The following reference material has been categorized by type of conjugate where it is appreciated that the principles disclosed for making the various types of disclosed conjugates are applicable in making any of the type of conjugates contemplated by this invention.

| CONJUGATE CATEGORY | REFERENCE |
| --- | --- |
| Plant lectin-Enzyme | Stavrianopoulus, J. Yang, |
| Concanavalin A-Acid | H. L., Kelker, N. E., |
| Phosphatase | European Patent |
| Concanavalin A-Glucose | Application No. 0 133 473, |
| Oxidase | 1985. |
| Concanavalin A-Horseradish | |
| Peroxidase | |
| Hormone-Enzyme | |
| Estrogen-Horseradish | Bosh, A. M. G., van Hell, |
| Peroxidase | H., Brands, J. A. M., van Weeman, B. K., Schuurs, A. H. W. M., "Methods for the Determination of Total Estrogens (TE) and Human Placental Lactogen (HPL) in Plasma of Pregnant Women by Enzyme Immunoassay (EIA)," Clin. Chem. 1975; 21:1009 |
| Insulin-Alkaline | Miedema, K., Boelhouwer, |
| Phosphatase | J., Otten, J. W., "Determination of Proteins and Hormones in Serum by an Immunoassay Using Antigen-Enzyme Conjugates", Clin. Chim. Acta. 1972; 40:187-192 |
| Cortisol-$\beta$-Galactosidase | Comoglio, S., Celada, F. "An Immunoenzymatic Assay of Cortisol Using E. coli $\beta$-Galactosidase as Label" J. Immunol. Methods. 1976; 10:161-170 |
| Nucleic Acid-Enzyme | |
| Oligonucleotide-Alkaline | Jablonski, E., Moonmaw, |
| Phosphatase | E. W , Tullis, R. H., Ruth, J. "Preparation of Oligodeoxynucleotide-Alkaline Phosphatase Conjugates and Their Use as Hybridization Probes", Nucl. Acid Res. 1986; 14:6115-28 |
| Oligonucleotide-Alkaline | Li, P., Medon, P. P., |
| Phosphatase | Skingle, D. C., Lanser, J. A., Symons, R. H., "Enzyme-linked Synthetic Oligonucleotide Probes: Non-Radioactive Detection of Enterotoxigenic *Escherichia coli* in Faecal Specimens", Nucl. Acid Res. 1987; 15:5275-87 |
| Single Stranded DNA- | Renz, M., Kurz, C., |

-continued

| CONJUGATE CATEGORY | REFERENCE |
| --- | --- |
| horseradish Peroxidase | "Colorimetric Methods for DNA Determination" Nucl. |
| Single Stranded DNA-alkaline Phosphatase | Acids Res. 1984; 12:3435-3444. |
| Lambda DNA-Horseradish Peroxidase | Downs, M. E. A., Warner, A. P. F., "Colorimetric Detection of Horseradish Peroxidase-Labelled DNA Using a New Chromogen System", Biotechnology Techniques 1987; 1:129-134 |
| Hapten-Enzyme Carboxymethylmorphine-lysozyme | Rubenstein, K. E., Schneider, R. S., Ullmann, E. F., "Homogeneous Enzyme Immunoassay, a New Immunochemical Technique", Biochem. Biophys. Res. Commun. 1972; 47:846-851 |
| Antibody-Enzyme | |
| IgG-Horseradish Peroxidase | Ishakawa, E., "Enzyme-Labeling of Antibodies" |
| IgG-Galactosidase | J. Immunoassay 1983; |
| IgG-Glucose Oxidase | 4:209-237 |
| IgG-Alkaline Phosphatase | |
| IgG-Horseradish Peroxidase | Wilson, M. B., Nakane, P. K., "Recent Developmemts in the Periodate Method of Conjugating Horseradish Peroxidase (HRPO) to Antibodies, pp 215-225 in Immunofluorescence and Related Staining Techniques, Knapp, W., Holubar, K., Wick, G., Eds. Elsevier/North Holland Biomedical Press, 1978. |
| IgG-Alkaline Phosphatase | Parkinson, A. J., Scott E. H., Muchmore, H. G., "Rapid Micromethod for Preparation of Enzyme-Antibody conjugates" J. Clin. Microbiol. 1982; 15: 737-739 |
| Anti-HCG-Horseradish Peroxidase | van Weeman, B. K., "Schuurs. Immunoassay Using Antibody-Enzyme Conjugates", FEBS Letters 1974; 43: 215-218 |
| Binding-Protein Enzyme | |
| Avidin-Alkaline Phosphatase | Matthews, J. A., Kricka, L. J., "Analytical |
| Avidin-$\beta$-Glactosidase | Strategies for the Use of DNA Probes", Anal. Biochem. 1988, 169:1-25 |
| Avidin-Horseradish Peroxidase | |
| Streptavidin-$\beta$-Galactosidase | |
| Streptavidin-Acid Phosphatase | |
| Streptavidin-Alkaline Phosphatase | |
| Streptavidin-Horseradish Peroxidase | |
| Protein A-Enzyme | Chantler, S. M., Clayton, A. L., "The Use of ELISA for Rapid Viral Diagnosis: Viral Antigen Detection in Clinical Specimens:, p. 286 Chapter 13 in ELISA and Other Solid Phase Immunoassays, Kemeny. D. M., Challacombe Eds., 1988 J. Wiley and Sons, Chichester |

A general technique for preparing protein-glycoprotein conjugates involves periodate oxidation of the carbohydrate moiety of the glycoprotein to produce aldehyde groups as described in P. Tijssen, "Practice and Theory of Enzyme Immunoassays, Vol. 15, Chapter II, pp 230–142, Laboratory Techniques in Biochemistry and Molecular Biology, R. H. Burdon and P. H. van Knippenberg Eds. Elsivier, Amsterdam, 1985. Additional references which are of interest for enzyme-conjugates are: V. Fert and A. Baret, J. Immunol. Method, (1990) 131 237–248; and BR Clark and E Engvall, in "Enzyme Immunoassay", ed. ET Maggio, CRC Press Inc., Boca Raton, 1980, 167–212).

There is a wide range for selection of suitable enzymes and substrates within the scope of the present invention. Enzyme and substrate choice will vary depending upon the type of assay (also referred to herein as assay format) in which the enzyme detection will occur. For example, certain assays are optimized if the reactants and products are soluble. Alternatively, other assay formats are optimized if the product of the enzyme-substrate reaction precipitates out of solution. Examples of different assay formats using different enzyme-substrate reactants are described herein and illustrate the wide range of assay formats to which the enzyme amplified lanthanide luminescence (EALL) of the present invention can be applied.

The advantageous differences of lanthanide luminescence measurement over normal fluorescence, and the advantageous differences resulting from using lanthanide luminescence combined with enzyme detection (as compared to other possible detection methods such as colorimetric, chemiluminescence, normal fluorescence) are discussed below.

In "normal" fluorescence, the normal fluorophore consists of a molecule which has a broad absorption spectrum, and a broad emission spectrum. The emission maximum is shifted 50–100 nm to longer wavelength from the position of the absorption maximum. Usually the emission is located somewhere within the region of the ultraviolet to green wavelengths. The lifetime of the emission is quite short, in the range of 1 ns to 1 $\mu$s.

These characteristics of normal fluorescence are also true of so-called "background" fluorescence coming from the other reagents in the assays, components of the sample being measured, solid supports used in the assay, etc. Thus conditions under which the "normal" fluorescence is measured are also optimum for measurement of the background. In addition, frequently scattered excitation light is also measured under the optimum measurement conditions. No further optimization of signal/background can be performed. This means that ultrasensitive detection in biological systems is frequently not possible using currently known assay formats.

A few fluorophores have been designed which possess one or both of the following desirable features:

(i) large Stokes shift in the emission, meaning shifts larger than 100 nm in emission maximum; typically in this case emission is in the yellow-red region. This facilitates filtering out of scattered excitation light.

(ii) longer emission lifetime than normal, i.e. >1 $\mu$s. This facilitates the use of inexpensive time-gated detection methods, which measure only the desired signal and not the background or scattered light.

However of all the fluorophore systems so far designed, only lanthanide chelates combine both these two properties (in a particularly optimum way because of the large Stokes shift and extremely long lifetime) in addition to:

(iii) narrow-band emission. This permits even better wavelength filtering, through the use of narrow-band filters, once again discriminating against broad background fluorescences.

It is the combination of these three features, in preferred embodiments of the present invention, which permit powerful discrimination against background signals, making ultrasensitive bioanalytical assays possible. The lanthanide chelates which have as lanthanide one of the trivalent ions europium, terbium, samarium or dysprosium can be considered as a class of compounds all possessing these three preferred features, and which can be identified as a single group. No other metal chelates possess all of these properties. There is no doubt that replacement of other fluorophore systems which have been used for enzyme-amplified detection with a lanthanide based system is a substantial improvement, replacing something which is impractical for sensitive detection in biological assays with a system which is practical as demonstrated herein.

A major difference resulting from the use of lanthanide based detection combined with enzymatic amplification is the ability of this detection system to respond to certain types of chemical changes between substrate and product to which other existing detection systems are not sensitive. These mainly include changes in chelating ability. Such changes can occur remote from the chromophoric group and need not affect the spectroscopic properties; hence they are generally not detectable by other methods. This substantially expands the list of enzymes which can be easily detected. This is particularly relevant when the method of the present invention is used to analyze biological samples for a particular enzyme. However, it is also useful in enriching the availability of other enzymes, for use as labels, which previously would have been unsuitable in many assay formats which would otherwise suffer from high backgrounds.

The spectroscopic and chelating properties of the substrate/product pair must be determined to be generally suitable; that is, the substrate is non-competitive with the product, for the enzymatic system and assay format of choice. The substrate/product pair selected will vary depending upon the nature of the assay (example heterogeneous or homogeneous), the possible presence of interfering contaminants in the sample and, possibly, other impinging factors. Numerous examples are provided herein such that one skilled in the art would understand the selection assessment which is made when selecting a suitable substrate/enzyme/product system.

More particularly, the relevant properties to be considered, when assessing the conversion of substrate to product and the selection of a suitable substrate/product pair, include:

(a) alteration of the position of the UV spectrum such that the substrate does not absorb the chosen excitation light efficiently while the product does;

(b) alteration of the position of the triplet level of the substrate such that the substrate does not transfer efficiently the excitation energy to the chelated lanthanide, while the product does; and (c) alteration of the chelating properties such that the substrate does not efficiently chelate the lanthanide while the product does.

The alteration of at least one, and preferably all three, of these properties by an enzyme in the present invention results in very efficient detection of the product molecule only, even in the presence of a very large excess of the selected non-competitive substrate molecule. Other more specific considerations may come to play once these initial three considerations have been assessed. When required, one skilled in the art would be able to make such determinations having the teachings of the present invention disclosure and accompanying Examples.

In the case of salicyl phosphate, all three of the above identified alterations occur upon enzymatic conversion of the substrate to its product. The UV maximum shifts from about 280 to 290 nm for the phosphate to about 300 to 310 nm for the dephosphorylated form. The triplet energy also shifts (items (a) and (b) tend to be strongly coupled). In addition, the phosphate group is located in the chelating site and its presence probably reduces the efficiency of chelate formation due to an alteration in geometry and blocking of the chelating site.

In the case of the HRP substrates the same observations, as described above for the salicyl phosphates, hold true for the most part. One difference is that the chelating ability is improved in the product by coupling two molecules which individually have fewer chelating groups. In addition, solubility should be substantially reduced by the increase in molecular weight rendering these substrates desirable for membrane formats.

Other substrates may demonstrate only one or two of the three beneficial alterations. For example, BCAHAP satisfies criteria (a) and (b), while HCAB.dee satisfies only criteria (c). The most successful substrate candidates will satisfy all three criteria.

The salicyl phosphate substrates are excellent examples of how variations in substrate substituents can alter the effectiveness of that particular substrate/product pair in different assay formats. If the structure of the substituent on the salicyl phosphate is chosen to be bulky and hydrophobic the mobility of both substrate and product are reduced, thereby increasing the likelihood of the product remaining in the vicinity of the enzyme which produced it over a period of several hours. The mobility of the product, in addition, is substantially reduced from that of the substrate because of the removal of the extremely hydrophilic, doubly charged phosphate group, to produce a phenol group which is uncharged under the conditions of the reaction. Alternatively, if the fluoro-derivative is the substituent this is the substrate of choice in soluble microwell assays. If a fluoro-derivative was used in a membrane format, the product would diffuse rapidly from the place where it was produced, eventually resulting in total loss of signal due to dilution and smearing of the signal. This molecule has been chosen for use in solution phase assays because it forms such a soluble product, resulting in better reproducibility in solution-phase formats. Less soluble products result in local hot-spots of signal, which are not desirable when homogeneity of the reaction mixture is required. In this instance, the replacement of the substituent tert-octyl by fluoro results not only in higher solubility but also higher luminescence.

DNA hybridization assays are an example of an assay format performed on membranes. Typically these membranes are modified nylon or nitrocellulose such that target DNA will bind efficiently and easily. In known membrane based DNA hybridization assays the presence of DNA is detected using some form of labeled reagent which generates a signal and the signal (e.g. radioactivity, chemiluminescence) is usually detected by some form of qualitative photography.

In preferred embodiments of the present invention it is recognized that the signal in membrane based DNA hybridization assays be located spatially on the membrane in the same place as the original DNA, as the original target DNA is frequently identified in some way by its location on the membrane. This means that the signal generating species should not migrate from the original location. At the same time it is recognized that the signal reagent must not be "too sticky" as this may result in a large amount of non-specific binding to the membrane thereby decreasing the sensitivity and selectivity of the assay results. Two lanthanide-luminescent-based detection methods have been developed for immunoassays in microwell formats which use direct labelling and which could be used for membrane based DNA hybridization assays. One such system is the EuroFluor S-labeled-protein/streptavidin conjugate developed by CyberFluor (RC Morton & EP Diamandis, Anal. Chem. 62 (1990) 1841-1845, EP Diamandis and RC Morton, J. Immunol. Meth. 112 (1988) 43-52), and the second uses europium-DTTA (diethylenetriamine tetraacetic acid -labeled antibody conjugates (I. Hemmila, Scand. J. Clin. Lab. Invest. 48 (1988) 389-400).

The disadvantage of the first method is that the reagents are sticky. The reagents therefore stick onto the nylon membrane where they should not, i.e. where there is no target species. The resultant nonspecific binding is far too high to give sensitive detection. Without the invention of different membranes, not currently in use in DNA hybridization assays, this system is impractical. In the second method, the method of developing the signal requires complete solubilization of a europium label into the enhancement reagent. The solubilization of the signal potentially results in its complete removal from the location in which it is generated, making membrane assays which require localization of signal impossible.

In the enzyme-amplified detection methods of the present invention an enzyme is located in the immediate vicinity of the target DNA after the hybridization reaction has occurred and the signal generating system is designed such that movement of the product of the enzymatic reaction away from the location of the bound enzyme is minimized. In preferred embodiments of the present invention the detection/quantitation method is devised such that the original substrate is quite soluble (thereby minimizing the risk of non-specific substrate binding to the membrane), but the product of the enzymatic reaction is substantially insoluble. While this is a general principle, it is necessary to tailor the design of the substrate/product pair specifically, based on the nature of the enzyme used and the type of chemical reaction chosen to form the product.

The salicyl phosphate derivatives which best fulfil the criteria for a membrane-based assay are essentially alkyl-derivatives having a hydrophobic substituent group in any one of positions 3, 4, 5 or 6 on the benzene ring thereby rendering the solubility and mobility of the product salicylic acid quite low.

Alternatively, the optimal salicyl phosphate derivatives for a solution assay, such as, those performed in microwells, replace the above-described hydrophobic substituent group with a small hydrophilic substituent group thereby resulting in a soluble product. In the case of a solution-based microwell format using FSAP the largest possible volumes are used in order to increase the amount of signal generated. These two particular systems, membrane based assay format and microwell assay format, are two examples of how signal development, assay and luminescence measurement conditions must be carefully optimized to make a practical system with high sensitivity.

The structure of the TOSAP/TOSA substrate/product pair and the conditions of the reaction, development and measurement have been carefully tailored for a membrane format in accordance with the following details.

The enzymatic reaction conditions have been optimized for the alkaline phosphatase enzyme conversion of substrate to product; the reaction is performed at pH 9, which is optimum for the AP enzyme, and is performed in the presence of a phosphate acceptor, tris buffer, which accelerates the rate of the reaction. The Tb:EDTA is not present during the enzymatic reaction, for three reasons: EDTA can inactivate the enzyme by chelating the Mg from the active site of the AP; Tb causes a slightly enhanced rate of nonspecific hydrolysis of the phosphate group causing increased backgrounds; and finally the solubility and mobility of the TOSA:Tb:EDTA complex is substantially higher than that of the TOSA by itself, which means it will diffuse excessively during the time taken for the enzymatic reaction (1 hr-overnight). The volume is minimized during the reaction to prevent excessive diffusion of the product.

The chemical conditions for detection of the product molecule have also been optimized. The optimum conditions for detection of the product molecule are at higher pH, namely around 12.5, with Tb:EDTA present. Hence, in order to detect the product TOSA, the conditions of the signal measurement are changed from those of the enzymatic reaction by adjusting the pH and adding Tb:EDTA, in order to optimize signal detection. Because the TOSA:Tb:EDTA is more soluble, the conditions for signal development must also be tailored to prevent diffusion of the product. This is done by reducing the volumes of solution used, and removing excess substrate solution, to prevent diffusion of signal during the measurement process.

The spectroscopic conditions of the time-resolved luminescence measurement are optimized in order to reduce background signal, which is generated by (i) the presence of Tb:EDTA and TOSAP:Tb:EDTA complexes in addition to the desired TOSA:Tb:EDTA complex; and (ii) background phosphorescence from the membrane.

This is performed by (i) choosing an excitation wavelength >320 nm (which selectively excites the TOSA:Tb:EDTA complex rather than any TOSAP:Tb:EDTA which may be formed); ii) by using a time gate from about 600–2000 μs, which selectively measures TOSA:Tb:EDTA rather than Tb:EDTA, which has a much shorter lifetime; and (iii) measuring at wavelengths >515 nm which reduces the background from the membrane itself.

The optimization of the enzymatic reaction conditions, the chemical conditions for detection of the product molecule and the spectroscopic conditions of the time-resolved luminescence (as described above for a membrane based assay format) which is necessary for a solution-based assay format, remain largely unchanged, except that instead of minimizing the volumes, larger volumes can be accommodated.

In accordance with an aspect of the present invention, a generalized structure for the substrate is depicted as follows:

FORMULA I

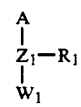

wherein $Z_1$ is a UV-absorbing aromatic chromophoric group containing one or more heteroatoms such as oxygen or nitrogen. Examples of suitable chromophores are aryloxy chromophores such as those derived from phenol, catechol, naphthol, 4-hydroxyacetophenone, 4-hydroxybenzophenone, and 7-hydroxycoumarin, and others such as benzoyl, phthaloyl, pyridine, and 1,10-phenanthroline.

A is one or more non-coordinating or poorly coordinating groups which can be enzymatically hydrolysed or oxidized to a strongly coordinating group such as a phenoxide anion, carboxylate, or amino group. Alternatively, or in addition, the hydrolysis or oxidation of A may alter the spectroscopic properties of $Z_1$ such that the excited state of $Z_1$ would be at the proper energy level to excite the lanthanide ion after the enzymatic reaction. Examples of such hydrolyzable functional groups include the following esters of $Z_1$: monophosphate ester, acyl ester, or sulfate ester; other hydrolyzable groups include amide, nitrile or glycoside. Examples of suitable oxidizable functional groups include an aldehyde, alcohol, or hydrazide group of $Z_1$.

$W_1$ is hydrogen or one or more groups which additionally coordinate a lanthanide ion and contribute to higher luminescence of the lanthanide chelate by increasing the equilibrium constant of formation between the lanthanide ion and the enzyme-amplified product or by occupying the coordination sites around the lanthanide resulting in removal or reduction of the number of coordinated water molecules. $W_1$ is directly attached to the chromophore or indirectly attached through carbon atoms. The enzymatic reaction may be allowed to proceed in the absence of lanthanide in which case the binding between $W_1$ and the lanthanide occurs only after the reaction. Examples of suitable coordinating groups of $W_1$ are the carboxylate, oxyanion, amino, hydroxyl, N,N-bis(carboxymethyl)aminomethyl, diethylenetriaminetetraacetic acid, polyoxo macrocycle, polyaza macrocycle and polyoxo-aza macrocycle.

$R_1$ is hydrogen or one or more groups which are unaffected by the enzymatic reaction and is present in order to optimize the performance of the substrate. $R_1$ is directly attached to the chromophore or indirectly through carbon atoms. $R_1$ may be a group which alters the excited state energy of the chromophore Z resulting in increased luminescence of the product. $R_1$ may also be a bulky hydrophobic substituent directly attached to the chromophore which causes the enzyme-amplified product to precipitate or become less soluble or less diffusive on a solid surface for assay applications such as dot blot, Southern blot, colony or plaque hybridization or Western blot. Examples of such substituents are phenyl, $C_2$ to $C_{20}$ alkyl, $C_1$ to $C_{20}$ alkyl substituted phenyl, halogenated phenyl, trifluoromethyl, trityl, tert-octyl, and cumyl groups.

More particularly, salicyl phosphates can be used as reagents for detection or quantitation of an analyte in a sample wherein the detection signal is luminescence from a lanthanide chelate and the said luminescent lanthanide chelate is formed by alkaline phosphatase-catalyzed conversion of the salicyl phosphate substrate. The salicyl phosphate substrate is depicted by the following general formula:

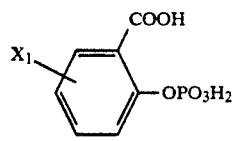

FORMULA II wherein $X_1$ is hydrogen, halogen, $C_2$ to $C_{20}$ alkyl, $C_2$ to $C_{20}$ aryl, $C_2$ to $C_{20}$ aryl containing at least one heteroatom, a heteroaromatic group of pyridine, furan, pyrrole and thiophene which are ring unsubstituted or ring substituted with $C_1$ to $C_{10}$ alkyl or halogen, trityl, 2,4-difluorophenyl. $X_1$ can be a substituent at any one of the 3, 4, 5 or 6 carbon atom positions on the benzene ring.

The following specific compounds of the salicyl phosphate family are novel compounds disclosed in accordance with an aspect of the present invention:

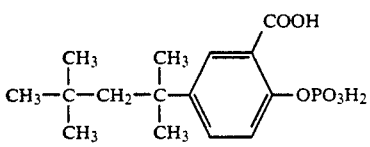

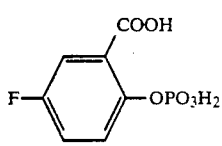

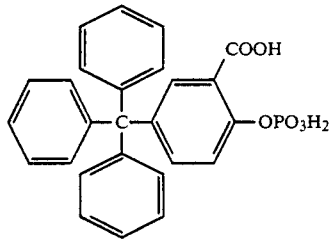

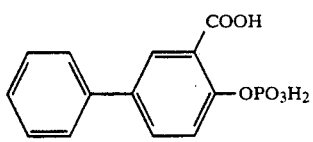

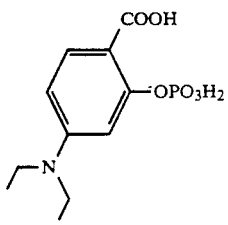

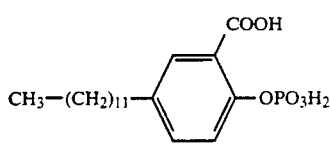

These substrates are useful as reactants in EALL.

Other preferred novel substrate compounds are of the BCAHAP family of AP substrates. These novel substrates have the general formula:

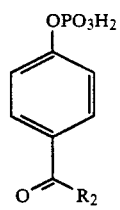

FORMULA III wherein $R_2$ is selected from commonly known chelating substituents, containing one or more amino, carboxylate, hydroxyl, or ether functionality, these functionalities being separated from the carbonyl group by at least one carbon atom. Examples of $R_2$ include a polyaza- or polyoxo- macrocycle, an aminopolycarboxylic acid or a polyaminocarboxylic acid. The compound BCAHAP is preferred wherein $R_2$ is N,N-bis(carboxymethyl)aminomethyl.

In accordance with another embodiment of the present invention novel substrates are provided for horseradish peroxidase (HRP) - catalyzed phenol coupling. These substrates for HRP-catalyzed phenol coupling can be depicted by the following general formula:

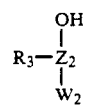

FORMULA IV wherein $Z_2$ is a UV-absorbing chromophore selected from the group consisting of benzene, naphthalene, and pyridine; $R_3$ is hydrogen or at least one group which is hydrophobic to limit thereby diffusion in an aqueous medium of said chelator or a group which alters the excited state energy of chromophore $Z_2$ resulting thereby in increased luminescence of said chelated lanthanide metal ion; $W_2$ is at least one group containing one or more coordinating groups selected from carboxylate, amino, oxyanion or oxo, preferably containing glutamyl, $\gamma$-glutamyl, tyrosyl, a polyaminocarboxylic acid, an aminopolycarboxylic acid, a polyaza macrocycle or a polyoxomacrocycle.

One general type of enzymatic reaction can be represented by the following scheme:

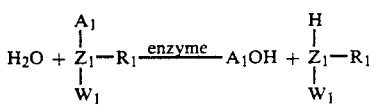

SCHEME I

In this scheme, $A_1$ is connected to $Z_1$ through a hydrolyzable bond in which one of the atoms is a nucleophilic group such as oxygen, nitrogen or sulfur which is part of $Z_1$. When hydrolyzed by the action of an enzyme, the products, consisting of the molecule $A_1OH$ (or its ionized form $A_1O^-$) and the lanthanide chelator $R_1$-$Z_1$H-$W_1$ or its basic form $R_1$-$Z_1$-$W_1$ are formed. A strongly luminescent lanthanide chelate is formed between $R_1$-$Z_1$-$W_1$ and a lanthanide ion such as $Eu^{+3}$, $Tb^{+3}$, $Sm^{+3}$, or $Dy^{+3}$. The increase in luminescence for the product chelate can occur, for example, as a result of the removal of a blocking group $A_1$ from a chelating atom contained in $Z_1$, or an alteration in the wavelength of absorption and energy levels due to an alteration of electron delocalization in the product, or a combination of the two effects. Examples of common enzymes which catalyze such a hydrolysis reaction include carboxylesterase (EC3.1.1.1), alkaline and acid phosphatase (EC3.1.3.1 and 3.1.3.2), β-galactosidase (EC3.2.1.23), arylsulphatase (EC3.1.6.1), arylamidase (EC3.5.1.13); for these enzymes the group $A_1OH$ produced respectively on hydrolysis are a carboxylic acid, phosphate, galactose, sulphate and carboxylic acid. $R_1$ and $W_1$ are as defined in Formula I.

The enzyme being assayed or used as label in an immunoassay or DNA hybridization assay can also promote a reaction represented by the following generalized scheme:

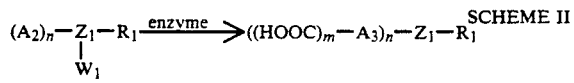
SCHEME II $Z_1$, $R_1$ and $W_1$ are exactly as described in Formula I. $A_2$ is a group which contains one or more groups $X_3$. $A_2$ is transformed by the action of the enzyme into $A_3(COOH)_m$ (or into COOH in the case that $A_2=X_3$), or the ionized form of the acid; m is the number of groups $X_3$ contained in each $A_2$, and n is the number of groups $A_2$ independently attached to $Z_1$. $X_3$ is a poorly coordinating group, which can either be hydrolysed by a hydrolytic enzyme in the presence of water, or oxidized by an oxoreductase enzyme in the presence of a suitable oxidizing agent, to the more strongly coordinating carboxylic acid anion $-COO^-$. For example, $X_3$ can be an ester group (COOR'), an amide group (CONHR') or a cyano group (CN) which would be hydrolysed by an esterase (e.g. EC3.1.1.1), amidase (e.g. EC3.5.1.13) or nitrilase (e.g. EC3.5.5.1) enzyme respectively. In addition, $X_3$ can be an aldehyde group (CHO) which can be oxidized to a carboxylic acid, for example, by the action of xanthine oxidase (EC1.2.3.2), or an alcohol group ($CH_2OH$) which can be oxidized in a two-step route, first to the aldehyde by the action of, for example, alcohol dehydrogenase (EC1.1.1.1), and then to the carboxylate by the action of aldehyde dehydrogenase (EC1.2.1.3). $X_3$ can also be a hydrazide group ($CONHNHR_2$), which can be oxidized to the carboxylate by a peroxidase (EC1.11.1.7) in the presence of hydrogen peroxide.

The above-mentioned enzyme can also promote a coupling reaction which can be represented by the following scheme:

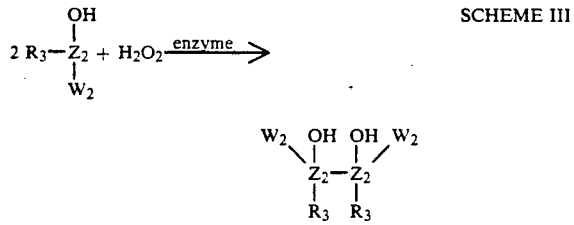
SCHEME III where $Z_2-OH$ is a phenolic chromophore such as a phenol or naphthol, $W_2$ is one or more metal ion chelating groups containing amino, carboxylate, hydroxyl, or ether functionalities, these functionalities being separated from $Z_2$ by at least one carbon atom. Examples of $W_2$ include a polyaza- or polyoxo- macrocycle, an aminopolycarboxylic acid or a polyaminocarboxylic acid. $R_3$ is exactly as defined for $R_3$ of Formula IV. The groups $W_2$ become geometrically situated to surround the lanthanide metal ion in the product chelator. The chelator is capable of forming lanthanide chelates with substantially increased luminescence because of an increase in the wavelength of UV absorption due to the coupling of two chromophoric groups or doubling of the number of coordinating atoms resulting in the exclusion of coordinated water molecules from the lanthanide ion or a combination of the two effects. The peroxidase-catalyzed formation of fluorescent 2,2'-biphenols from non-fluorescent phenolic substrates in the presence of hydrogen peroxide is a well-known example of such a coupling reaction.

$W_2$ is directly attached to the chromophore or indirectly attached through carbon atoms. The preferred $W_2$ group are amino acid-bearing moieties such as glutamyl, γ-glutamyl and tyrosyl group. $W_2$ can also be carboxylate, oxyanion, amino, hydroxyl, aminopolycarboxylic acid, polyoxo- or polyaza- macrocycles.

$R_3$ is hydrogen or one or more groups which is unaffected by the enzymatic reaction and is present in order to optimize the performance of the substrate. $R_3$ is directly attached to the chromophore or indirectly through carbon atoms. $R_3$ may be a group which alters the excited state energy of the chromophore $Z_2$ resulting in increased luminescence of the product. $R_3$ may also be a bulky hydrophobic substituent directly attached to the chromophore which causes the enzyme-amplified product to precipitate or become less soluble or less diffusive on a solid surface for applications such as dot blot, Southern blot, colony or plaque hybridization or Western blot. Examples of such substituents are fluoro, phenyl, alkyl-substituted phenyl, halogenated phenyl, trifluoromethyl, trityl, tert-octyl, and cumyl groups.

Another enzymatic reaction which can be used as basis for lanthanide fluorometric detection is of the following type:

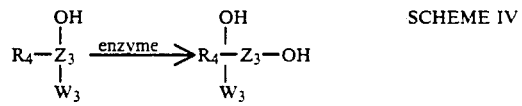
SCHEME IV $Z_3-OH$ is an aromatic hydroxy compound and $-Z_3-(OH)_2$ is an ortho- or para- dihydroxy aromatic compound such as a substituted catechol. Such reactions usually require oxygen and reduced NAD or NADP and are exemplified by the action of phenol 2-monooxygenase (EC 1.14.13.7), p-hydroxybenzoate hydroxylase (EC 1.14.13.2) and 2,6-dihydroxypyridine 3-monooxygenase (EC 1.14.13.aa). Ortho-dihydroxy aromatic compounds usually form lanthanide chelates with high formation constants and their excited states can have the proper energy for transfer to the lanthanide ion; formation of a paradihydroxy compound can alter the spectroscopic properties of the chromophore sufficiently to cause increased energy transfer for the product chelate.

These illustrated reaction types are not intended to be exhaustive, but are intended to demonstrate a variety of possible enzymatically catalyzed chemical reactions which can be utilized to produce highly luminescent lanthanide chelates.

Another aspect of the present invention provides a test kit for use in a variety of assay formats for the detection of luminescence emitted from an excited lanthanide metal chelate associated with a particular analyte. In this manner the test kit provides a means for detecting, possibly for the purpose of quantitating, a specific analyte. In accordance with a preferred embodiment of the invention the kit contains:
- a) selected substrate of the group represented by one of Formulas I, II, III or IV;
- b) lanthanide metal ion and optionally one or more co-chelators typically in concentrated stock solution; and
- c) where appropriate, membranes, microtitre wells or test tubes.

More particularly, the kit may be furnished as follows:
- a) selected substrate (typically dry reagent or concentrated stock solution);
- b) lanthanide ion salt (typically in concentrated stock solution, may be combined with a));
- c) where appropriate, co-chelator for enhancement of luminescence of lanthanide ion chelate (typically in concentrated stock solution; may be combined with b));
- d) protocol for the relevant assay format; and
- e) where appropriate, membranes, microtitre wells or test tubes.

The kit may contain, in addition, one or more buffer solutions for reconstitution of dry reagents or concentrated stock solutions which may provide after reconstitution a pH giving optimal reagent stability or optimal measurement conditions, an enzyme labelled detection probe such as enzyme labelled avidin or streptavidin, or alkaline phosphatase labelled oligonucleotide, or biotinylated probe. One embodiment of the kit contains reagents for use in hybridization assays. Another embodiment of the kit includes reagents and materials for performing the enzyme labelling of the relevant detection probe by the user.

Further details of the preferred embodiments of the invention will be understood from the following examples which are understood to be non-limiting with respect to the appended claims.

EXAMPLE 1. SALICYLALDEHYDE: XANTHINE OXIDASE SUBSTRATE

Xanthine oxidase can oxidize a large number of aldehydes in the presence of oxygen to the corresponding acid. Salicylaldehyde (SAld) is oxidized to salicylic acid (SA) by xanthine oxidase according to the following reaction scheme:

SCHEME V

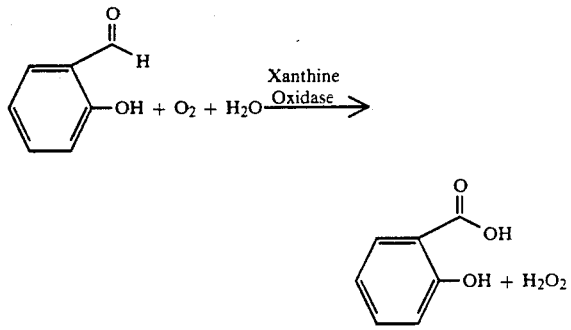

A stock solution of 0.1M SAld in ethylene glycol dimethyl ether was prepared. From this, an assay solution of $2 \times 10^{-4}$M SAld in 0.01M Hepes buffer pH 7.5 was prepared for assaying with xanthine oxidase (XOD, EC1.1.3.22) (Sigma, from bovine milk, 0.1 units/6 µL, in 2.3M $(NH_4)_2SO_4$, 0.02% sodium salicylate). 1 mL samples corresponding to ten-fold dilutions of enzyme from 0.1 U/mL to $10^{-5}$ U/mL were prepared in 0.01M Hepes pH 7.5 by serial dilution from the most concentrated sample as well as a 0 U/mL sample. To one half of each sample was added 0.5 mL of assay solution, while to the other half was added 0.5 mL of buffer; the resulting solutions contained $5 \times 10^{-2}$, $5 \times 10^{-3}$, $5 \times 10^{-4}$, $5 \times 10^{-5}$, $5 \times 10^{-6}$ and 0 U/mL of XOD, and 0 or $1 \times 10^{-4}$M SAld. Samples were left in acrylic UV-grade spectrophotometer cuvettes for 30 minutes at 22° C., and the reaction was terminated by addition of 300 µL of $0.33 \times 10^{-3}$ M ethylenediaminetetraacetic acid (EDTA), $0.33 \times 10^{-3}$ M $TbCl_3$, 0.33M NaOH, to make a final concentration of $8 \times 10^{-5}$M EDTA and $Tb^{+3}$, and 0.08M NaOH. The SA produced is thus quantitated as the Tb:SA:EDTA 1:1:1 complex as described previously (NS Poluektov, LA Alakaeva and MA Tischenko, Zh. Anal. Khim (1973) 28 1621-3 and I Hemmila, Anal. Chem. (1985) 57 1676-81). The Tb luminescence was read on a SPEX Fluorolog 212 spectrofluorimeter in pulsed phosphorimeter mode, (SPEX Industries, Inc., Edison, N.J.) using front-face pulsed excitation, with excitation at 320 nm, emission at 545 nm, bandwidths 14 nm, time delay 0.1 ms, and collection time window 2 ms. As illustrated in FIG. 1, a nearly linear (except at the highest concentration of XOD) relationship between Tb luminescence signal from the 1:1:1 Tb:SA:EDTA complex and [XOD] was obtained, once small background signals were subtracted (backgrounds were obtained from measurements on samples containing no XOD or no SAld; limit of noise is estimated from error on background measurements). The limit of detection of XOD under these conditions is approximately $5 \times 10^{-6}$ U/mL, without attempts at optimization. A radioactive method using $^{14}$C-labeled xanthine as substrate gives a detection limit of about $2 \times 10^{-7}$ U/mL [T. M. Dougherty, (1976) Anal. Biochem. 74 604-8]. A commonly used colorimetric method [described in H. U. Bergmeyer, Methods of Enzymatic Analysis, Vol. III 3rd ed. (1983) Verlag Chemie, Weinheim] gives a detection limit of $5 \times 10^{-4}$ U/mL, which is not sufficiently sensitive to measure a normal value in most cases. The method disclosed is thus superior to accepted nonisotopic methods and competitive with existing isotopic methods.

EXAMPLE 2. 4-HYDROXY-3-[N,N-BIS(CARBOXYMETHYL)-AMINOMETHYL]BENZOPHENONE DIETHYL ESTER (HCAB.dee): ESTERASE SUBSTRATE The synthesis of 4-hydroxy-3-[N,N-bis(carboxymethyl)aminomethyl]benzophenone diethyl ester was performed as follows.

To a stirred slurry of iminodiacetic acid (10 g, 0.075 mole) in absolute ethanol (500 mL) was added 5 mL concentrated sulfuric acid. The resulting clear solution was refluxed for 20 hrs under a Sohlet extractor with a thimble containing anhydrous $MgSO_4$ which was replaced twice during the duration of the reaction. After cooling to room temperature, the solution was concentrated in vacuo to an oil which was dissolved in about 400 mL ether. The organic layer was washed with 400 mL cold saturated aqueous $K_2CO_3$, dried over anhydrous $Na_2SO_4$, and concentrated in vacuo to produce a viscous liquid. The product was distilled at 2 torr at 78°-85° C. to produce 11 g (77% yield) of diethyliminodiacetate. $^1$H NMR in CDCl$_3$: δ1.3 triplet (6H), δ2.1 singlet (1H), δ3.5 singlet (4H), δ4.2 quartet (4H). IR KBr plates 2980, 1740, 1450, 1375, 1190, 1030, 770 cm$^{-1}$.

Aqueous formaldehyde (0.42 mL of 37% soln, 5.6 mmol) was added to a solution of diethyliminodiacetate (1.05 g, 5.6 mmol) in 5 mL ethanol. Removal of solvent in vacuo, addition of 5 mL ethanol, and concentration in vacuo produced a liquid residue to which was added 4-hydroxybenzophenone (0.56 g, 2.8 mmol). The resulting mixture was heated at 115° C. with stirring for 6 hr in an oil bath. Volatile components were removed by vacuum evaporation to produce a liquid residue. Flash chromatography through a silica gel column using hexane-ethyl acetate as eluting solvent produced 0.92 g (55 % yield) pure 4-hydroxy-3-[N,N-bis(carboxymethyl)aminomethyl]benzophenone diethyl ester (HCAB dee). $^1$H NMR in CDCl$_3$: δ1.27 (t, 6H), δ3.52 (s, 4H), δ4.13 (q, 4H), δ3.95 (s, 2H), δ6.83 (d, 1H), δ7.27-7.77 (m, 8H). IR KBr plates: 1595, 1605, 1740, 3150-3400 cm$^{-1}$.

The enzymatic reaction illustrated below consists of hydrolysis of one or both ester groups in the vicinity of neutral pH. Removal of the second ester group is probably strongly inhibited by the production of charged species as a result of removal of the first group. The product is a stronger chelating agent due to the additional coordinating carboxyl group(s), and is probably capable of forming both 1:1 complexes with Er$^{3+}$ (illustrated below) as well as higher order complexes with up to three product molecules acting as ligands.

SCHEME VI

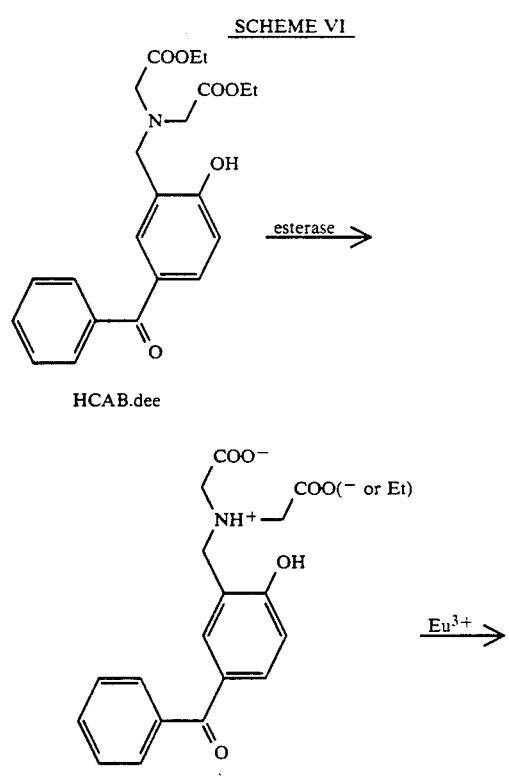

HCAB.dee

-continued
SCHEME VI

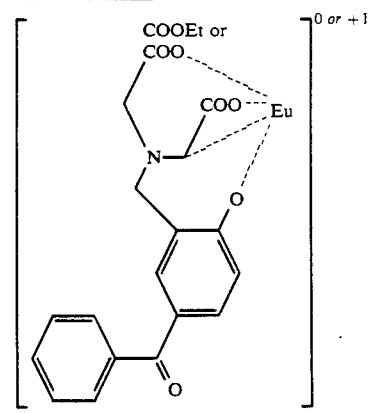

A 1.00×10$^{-3}$M stock solution of HCAB.dee was prepared in ethylene glycol dimethyl ether. From this stock solution, an assay solution of 10$^{-5}$M HCAB.dee in 0.01M tris buffer pH 8.0 was prepared. To 1 mL of assay solution was added 1 μL of pig liver esterase (PLE, EC 3 1.1.1) (Sigma, 3 units/μL in 3.2M (NH$_4$)$_2$SO$_4$), and from this solution 10-fold dilutions were made in assay solution, corresponding to 3, 0.3, 0.03, 0.003 U PLE/mL final concentration, in addition to a blank (0 U PLE/mL). The samples were allowed to react at 22° C. for 30 minutes, and then 1 μL of each solution was spotted in triplicate onto nylon membrane (Zetabind ™, AMF Cuno) and dried. The membrane was subsequently soaked for 5 minutes in a solution of 10$^{-5}$M EuCl$_3$ in 0.1M borate buffer pH 10.0 and then dried. Eu luminescence was observed by eye by illuminating the sample with a 366 nm UV lamp (Model UVL-21 Blak Ray ®) and observing through a 570 nm cut-off filter. The samples containing ≧0.03 units/mL gave signals observably higher than background, corresponding to detection of 0.1 fmol of PLE in 1 μL. Background signals were due to the presence of Eu-catalyzed hydrolysis of HCAB.dee during development of the signal, resulting in a luminescent product with Eu; no background signal was observed in the absence of substrate.

EXAMPLE 3. SALICYL-β-D-GALACTOSIDE: β-GALACTOSIDASE SUBSTRATE

The synthesis of salicyl-β-D-galactoside (Sal-gal) was performed as follows. To a stirred solution of methyl salicylate (0.304 g, 0.002 mol) in 5 mL absolute ethanol was added 0.96 mL of 5% sodium ethoxide (2.20M) in ethanol solution under argon. The sodium phenolate salt precipitated immediately as a white solid. The volatile components were removed on a rotary evaporator and then the solid was dried by addition of distilled pyridine followed by vacuum evaporation.

To a solution of methyl salicylate sodium salt (0.002 mol) in 10 mL dry distilled DMF was added with stirring under argon acetobromo-β-D-galactose (Sigma) (0.823 g, 0.0020 mol) in 10 mL DMF. The reaction was allowed to proceed with stirring under argon at room temperature for 9 days. The mixture was filtered through a sintered glass funnel and the filtrate was concentrated in vacuo to produce a solid residue. The product was dissolved in dichloromethane:methanol and then chromatographed on a flash silica gel column with 98% dichloromethane: 2% triethylamine as eluting solvent. The fractions containing the product with $R_f=0.60$ were pooled and then concentrated to produce 0.50 g (52% yield) of salicyl tetra-O-acetyl-β-D-galactoside methyl ester. The product was recrystallized from ethyl acetate-toluene containing a small amount of hexane to produce 83 mg of pure product. Mp=110°-112° C. $^1$H NMR in CDCl$_3$: δ1.95 (s, 3H), δ2.0 (s, 6H), δ2.1 (s, 3H), δ3.8 (s, 3H), δ4.1 (m, 2H), δ4.9-5.6 (m, 4H), δ6.8-7.9 (m, 4H). IR KBr disk: 2900-3000, 1750, 1710, 1605, 1495, 1460, 1375, 1315, 1230, 1070, 965, 775 cm$^{-1}$.

A stock solution of $5\times10^{-3}$M salicyl-β-D-galactoside was prepared by stirring a solution of salicyl tetra-O-acetyl-β-D-galactoside methyl ester (4.82 mg, $1\times10^{-5}$ mol) in 2 mL 0.1M KOH in methanol with heating in an oil bath at 70° C. for 3 hrs. Thin layer chromatography on C18 silica plates with 80% methanol:20% water as eluting solvent showed complete conversion of the salicyl tetra-O-acetyl-β-D-galactoside methyl ester ($R_f=0.66$) to salicyl-β-D-galactoside potassium salt ($R_f=0.81$). Both TLC spots absorbed 254 nm UV light indicating presence of an aromatic ring and acquired a green-gray colour after staining with anisaldehyde-ethanol-sulfuric acid staining reagent, indicating presence of a sugar.

The enzymatic reaction for the Sal-gal/galactosidase system is:

SCHEME VII

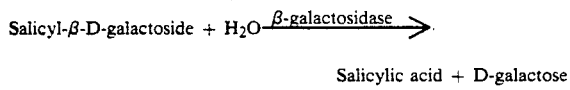

Salicylic acid + D-galactose and the salicylic acid (SA) can be measured (as outlined in Example 1) as the Tb:SA:EDTA complex.

To a solution of $1\times10^{-4}$M sal-gal in 0.1M formate buffer pH 3.5 was added 1 unit of β-galactosidase (EC 3.2.1.23, Sigma, from Jack Bean, 8.7 U/mL in 3M (NH$_4$)$_2$SO$_4$, 25 mM sodium citrate pH 5.5), and absorption spectra were measured at intervals. Over a period of 10 minutes, complete conversion was observed from a species absorbing with a maximum at 277 nm, $\epsilon=2100$M$^{-1}$cm$^{-1}$, to a species absorbing at 296 nm, $\epsilon=3900$M$^{-1}$cm$^{-1}$, showing complete conversion from the Sal-gal to SA.

Figure 2A:
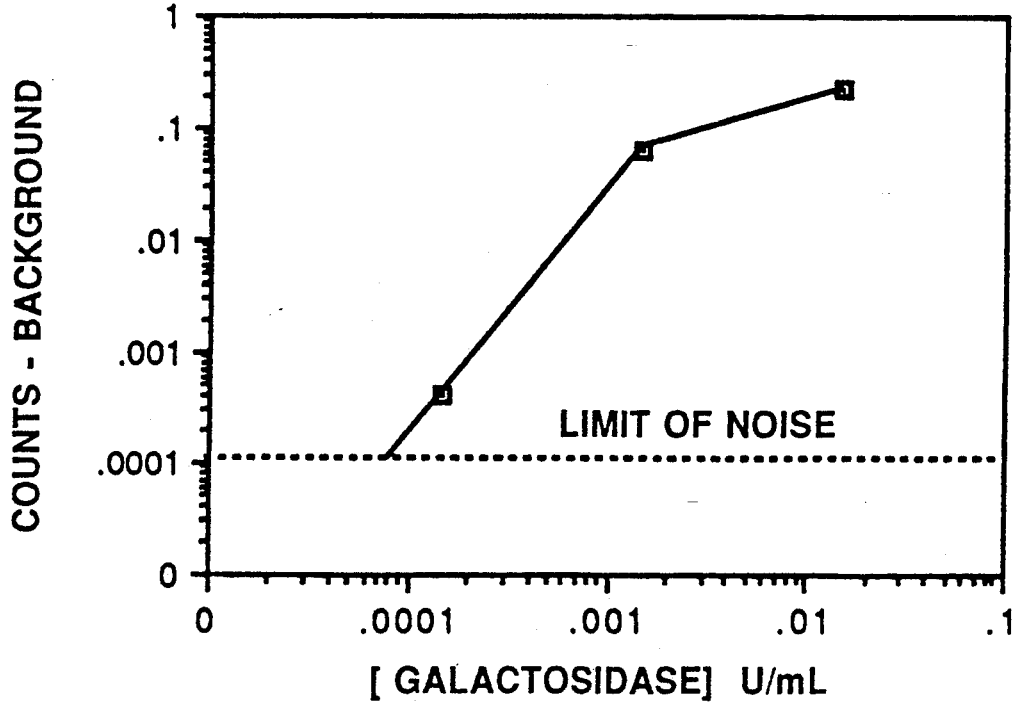
FIGS. 2a and 2b illustrate the determination of β-galactosidase using salicyl β-D-galactoside as substrate, as observed by measurement of the luminescence of Tb:salicylic acid:EDTA complex from the SA produced by the enzymatic reaction: a) 1.0 mL samples, measured on a SPEX ® fluorometer; b) 100 μL samples measured on a CyberFluor 615 Immunoanalyser ®.

Serial dilutions of β-galactosidase were prepared in 0.01M formate buffer pH 3.5, corresponding to concentrations of enzyme of 0.03, 0.003, 0.0003, and 0 U/mL, total volume 1 mL. To one half of each sample was added 0.5 mL of assay solution consisting of $2\times10^{-4}$M Sal-gal in 0.01M formate buffer pH 3.5, while to the other half was added 0.5 mL of buffer alone; the resulting solutions contained 0.015, 0.0015, 0.00015, or 0 units/mL of enzyme and 0 or $1\times10^{-4}$M Sal-gal. Samples were left in acrylic UV-grade spectrophotometer cuvettes for 30 minutes at 22° C., and the reaction was terminated by addition of 300 μL of $0.33\times10^{-3}$M EDTA, $0.33\times10^{-3}$M TbCl$_3$, 0.33M NaOH, to make a final concentration of $8\times10^{-5}$M EDTA and Tb, and 0.08M NaOH. Tb luminescence was read on a SPEX Fluorolog 212' spectrofluorimeter in pulsed phosphorimeter mode, (SPEX Industries, Inc., Edison, N.J.) using front-face pulsed excitation, with excitation at 320 nm, emission at 545 nm, bandwidths 14 and 7 nm respectively, time delay 0.1 ms, and collection time window 2 ms. FIG. 2a shows the signal (with background, from sample containing no enzyme, subtracted; the limit of noise is estimated based on the noise on the background) as a function of concentration of enzyme, giving a detection limit of approximately $10^{-4}$ U enzyme/mL under these conditions. The nonlinearity at high enzyme concentration is due to almost complete conversion of Sal-gal to salicylic acid as judged by comparison with a known concentration of salicylic acid.

Figure 2B:
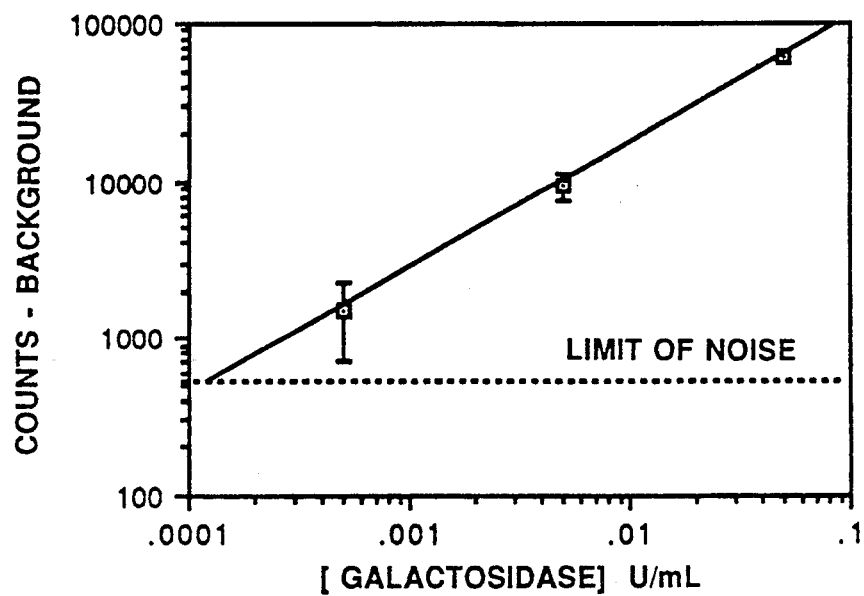

Ten-fold serial dilutions of β-galactosidase were prepared in triplicate in white microtiter wells (Dynatech, Microlite) containing a solution of 100 μl of $1\times10^{-4}$M Sal-gal in 0.01M formate buffer pH 3.5. After 40 minutes, to each well was added a total of 40 μL solution containing Tb, EDTA and 2 μmol NaOH, to make a final concentration of $8\times10^{-5}$M Tb and EDTA, and a final pH of 12. The wells were read using a CyberFluor 615 Immunoanalyser (CyberFluor Inc., Toronto, Canada) which uses 337 nm pulsed N$_2$ laser excitation, and measures integrated gated emission at 615 nm, 0.2-0.6 ms after excitation, under which conditions only Tb luminescence will be observed for these samples. The results for signal (with background subtracted, as calculated from the sample containing no enzyme; the limit of noise is estimated based on the standard deviation of the background) are illustrated in FIG. 2b, showing a detection limit of approximately $5\times10^{-3}$ U/mL, or $5\times10^{-4}$ U/well, under these conditions.

EXAMPLE 4.
4,5-DIHYDROXY-1,3-BENZENEDISULFONIC ACID DIACETATE: ESTERASE SUBSTRATE 4,5-Dihydroxy-1,3-benzenedisulfonic acid (DBDA) disodium salt was converted to the free disulfonic acid by passage of its aqueous solution through a Bio-Rad AG 50 W-X8 analytical grade cation exchange resin in the hydrogen form. The resulting solution was neutralized to pH 7 by addition of 40% aqueous tetra-n-butylammonium hydroxide. Removal of the solvent in vacuo yielded DBDA bis(tetra-n-butylammonium) salt as a white solid. Traces of water were removed by addition of dry pyridine followed by vacuum evaporation. A mixture of the solid (2.5 g, $3.3\times10^{-4}$ mole) and distilled acetic anhydride (5 mL, 0.053 mole) was heated with stirring in an oil bath at 100° C. in a flask fitted with a drying tube. After cooling to room temperature, the excess acetic anhydride was removed by vacuum distillation. The solid residue was dried in high vacuum to produce 0.306 g of crude product. Recrystallization from acetone-toluene produced 125 mg of pure white solid product, DBDA diacetate bis(tetra-n-butyl ammonium) salt. Mp=165°-167° C. Concentration of the mother liquor produced a second crop (36 mg). $^1$H NMR: δ0.9-2.0 multiplet (56H), δ2.3 singlet (6H), δ3.2 broad triplet (16H) δ7.3 doublet (1H), δ7.9 doublet (1H). IR KBr disk 3440, 2960, 2880, 1775, 1490, 1370, 1220, 1090, 1040, 900, 650 cm$^{-1}$.

The enzymatic reaction involves the deacetylation of DBDA diacetate. The Tb luminescence produced as a result of the complexation of the product with Tb could be observed during the reaction, according to the scheme shown below; most probably at least 1:1 and 1:2 Tb:DBDA chelates, whose luminescence has been previously described (I Hemmila, Anal. Chem. (1985) 57 1676-81) are formed under the conditions of the measurement.

SCHEME VIII

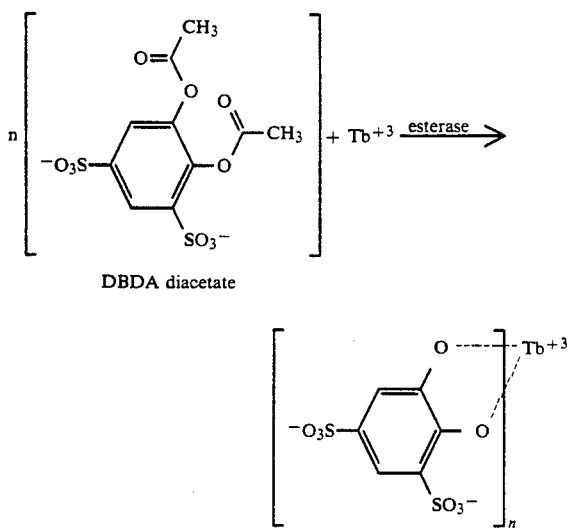

DBDA diacetate

A 0.005M stock solution of DBDA bis(tetra-n-butylammonium) salt in N,N-dimethylformamide was prepared prior to the UV spectral and fluorometic measurements. The UV spectrum of the diacetate in 0.1M Tris pH 8.0 showed maxima at 271 nm ($\epsilon=1150 M^{-1} cm^{-1}$) and 278 nm ($\epsilon=1070 M^{-1} c^{-1}$). Addition of pig liver esterase (PLE, EC 3.1.1.1) to the solution caused a fairly rapid conversion to the DBDA spectrum with $\lambda_{max}$ at 260 nm ($\epsilon=6080 M^{-1} cm^{-1}$) and at 302 nm ($\epsilon=4700 M^{-1} cm^{-1}$) indicating removal of the acetyl groups by enzymatic hydrolysis.

Figure 3:
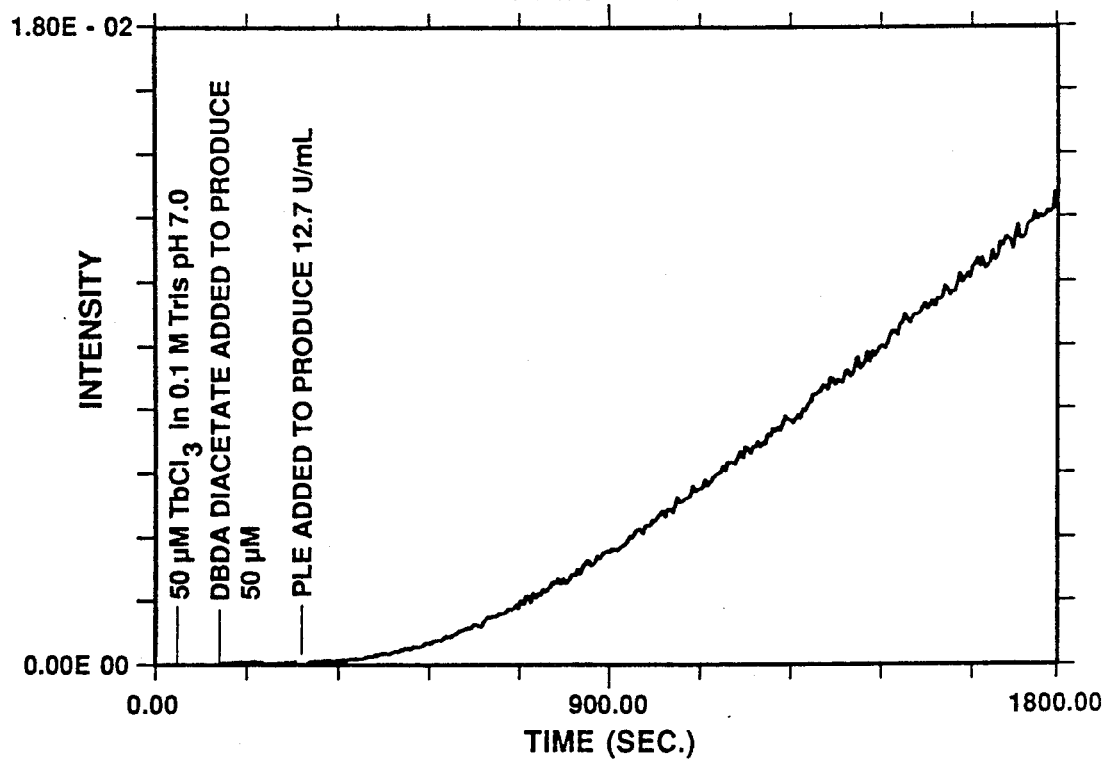
FIG. 3 illustrates the production of Tb:DBDA (stoichiometry 1:1 and/or 1:2) complexes by the action of esterase on DBDA diacetate in the presence of Tb, as observed by the increase in Tb luminescence upon addition of PLE.

The effect of the addition of 25.4 units of PLE to a solution containing an initial concentration of $5\times10^{-5}$ M DBDA diacetate and $5\times10^{-5}$ M TbCl$_3$ in 0.1M Tris pH 7.0 was monitored on the SPEX fluorometer in the pulsed phosphorescence mode with the excitation and emission monochromators set at 310 nm and 550 nm, respectively, with a delay of 100 μs and a collection time window of 2 ms. The luminescence signal was negligible before addition of enzyme but increased gradually (FIG. 3) due to the reaction described above.

EXAMPLE 5.
3,5-BIS[N,N-BIS(CARBOXYMETHYL)AMINOMETHYL]BENZOPHENONE-4-PHOSPHATE (HBCABP): ALKALINE PHOSPHATASE SUBSTRATE

The alkaline phosphatase substrate HBCABP was prepared according to the synthetic scheme illustrated below.

Aqueous formaldehyde (0.707 mL of 37% soln, 9.4 mmol) was added to a solution of diethyl iminodiacetate (1.78 g, 9.4 mmol) in 5 mL ethanol. Removal of solvent in vacuo, addition of 5 mL ethanol, and concentration in vacuo produced a liquid residue to which was added 4-hydroxybenzophenone (0.62 g, 3.15 mmol). The resulting mixture was heated at 115° C. with stirring for 6 hr in an oil bath. Volatile components were removed by vacuum evaporation to produce a liquid residue. Flash chromatography through a silica gel column using 4:1 hexane-ethyl acetate mixture as eluting solvent produced 1.23 g (65 % yield) pure 4-hydroxy-3,5-bis-[N,N-bis(carboxymethyl)aminomethyl]benzophenone tetraethyl ester (HBCAB.tee). $^1$H NMR in CDCl$_3$: δ1.27 (t, 12H), δ3.57 (s, 8H), δ3.90–4.77 (m, 12H), δ7.27–7.76 (m, 8H). IR KBr plates: 1590, 1605, 1655, 1740, 3150–3400 cm$^{-1}$.

SCHEME IX

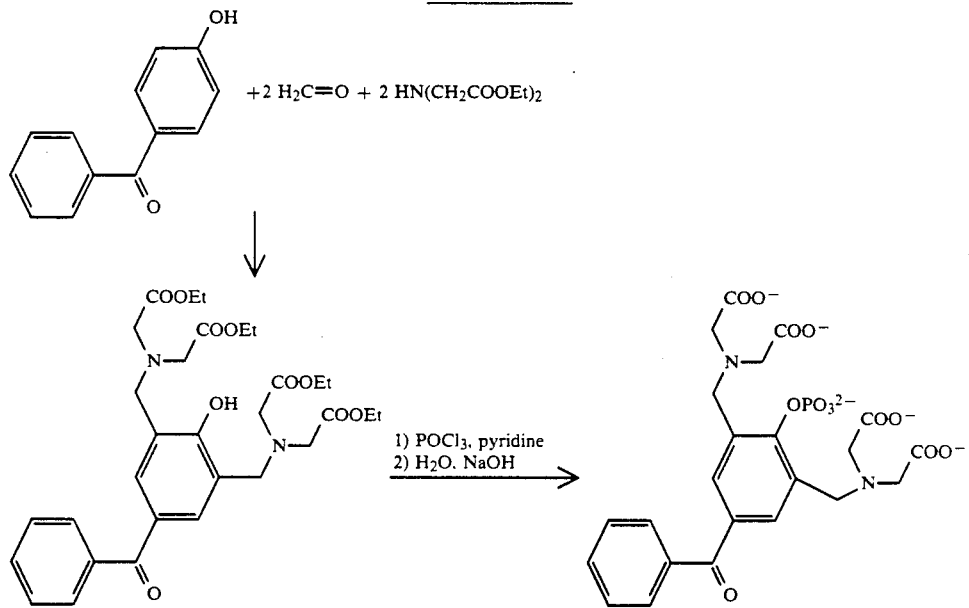

To a stirred solution of distilled phosphorus oxychloride (40 μL, $4.3\times10^{-4}$ mole) in 2 mL dry pyridine was added a solution of HBCAB.tee (0.214 g, $3.6\times10^{-4}$ mole) in 2 mL dry pyridine with stirring under argon. The reaction was allowed to proceed overnight at room temperature with stirring under argon. Cold water (2 mL) was added to hydrolyze the phosphorochloridate groups. Aqueous NaOH (0.54 mL of 5M soln) was added to form the phosphate disodium salt. The volatile components were removed on a rotary evaporator to produce a solid residue. To complete the hydrolysis of the ethyl ester groups, the product was redissolved in 5 mL water and 5M NaOH solution was added gradually until the pH stabilized at 12.7. Removal of solvent by vacuum evaporation produced 0.31 g of a yellow solid. IR in KBr disk showed a carboxylate salt band at 1600 cm$^{-1}$ and no ester carbonyl band at 1740 cm$^{-1}$. The 500 MHz $^1$H NMR of the crude product in D$_2$O indicated a mixture of compounds with aromatic protons at $\delta$7.4–7.9, a water peak at $\delta$4.6, methylene protons at $\delta$3.6–3.9, and methylene protons at $\delta$2.9–3.1.

The product HBCABP was purified by preparative anion exchange chromatography through a Pharmacia FPLC Mono Q HR 5/5 column using a linear (0.2M→0.5M) NaCl gradient containing 0.01M NaOH over a period of 15 min with UV absorbance monitoring at 254 nm. The product which eluted at 0 38M NaCl was the largest of five major fractions. The pooled fractions containing purified HBCABP were neutralized to pH 10 by addition of sodium bicarbonate solution and stored at 4° C. A portion of the solution was concentrated to dryness to produce a white solid whose D$_2$O solution showed a single $^{31}$P NMR peak at 0.28 ppm relative to the phosphoric acid standard.

The enzymatic reaction of alkaline phosphatase on HBCABP, and the subsequent formation of Eu:HBCAB chelate, whole luminescence has been reported previously (U.S. Pat. No. 4,637,988, Hinshaw et al.) is depicted in the scheme below:

0.5 mM, respectively, also caused hydrolytic dephosphorylation of HBCABP at pH 8.5 in the absence of AP to form the metal chelates with $\lambda_{max}$ at 322 nm. It was further observed that the metal-ion catalyzed hydrolysis is much slower (half life approx. 24 hrs) in carbonate buffer pH 11 where the enzyme has very little activity.

To demonstrate alkaline-phosphatase amplification of europium luminescence, it was necessary to allow the enzymatic reaction to proceed at pH 8.5 in the absence of any heavy metal ions and then to measure the luminescence of the Eu-HBCAB chelate at pH 11. Ten 1 mL solutions containing varying concentrations (0.019 unit/mL to 10 units/mL) of alkaline phosphatase in 0.025M Tris pH 8.5 were prepared in clear polystyrene cuvettes. HBCABP solution was added to each solution to produce an initial substrate concentration of 10 $\mu$M and then the solutions were incubated for 1 hr at room temperature (22° C.) to allow enzymatic dephosphorylation to proceed. Carbonate buffer was added to each solution to produce a carbonate concentration of 0.1M and bring the pH to 11. Europium chloride was added to produce a concentration of 10 $\mu$M Eu$^{+3}$. The time-resolved integrated luminescence of the resulting solutions was measured on the SPEX fluorometer with the excitation and emission monochromators set at 330 nm and 615 nm, respectively, with a time delay of 100 $\mu$s

SCHEME X

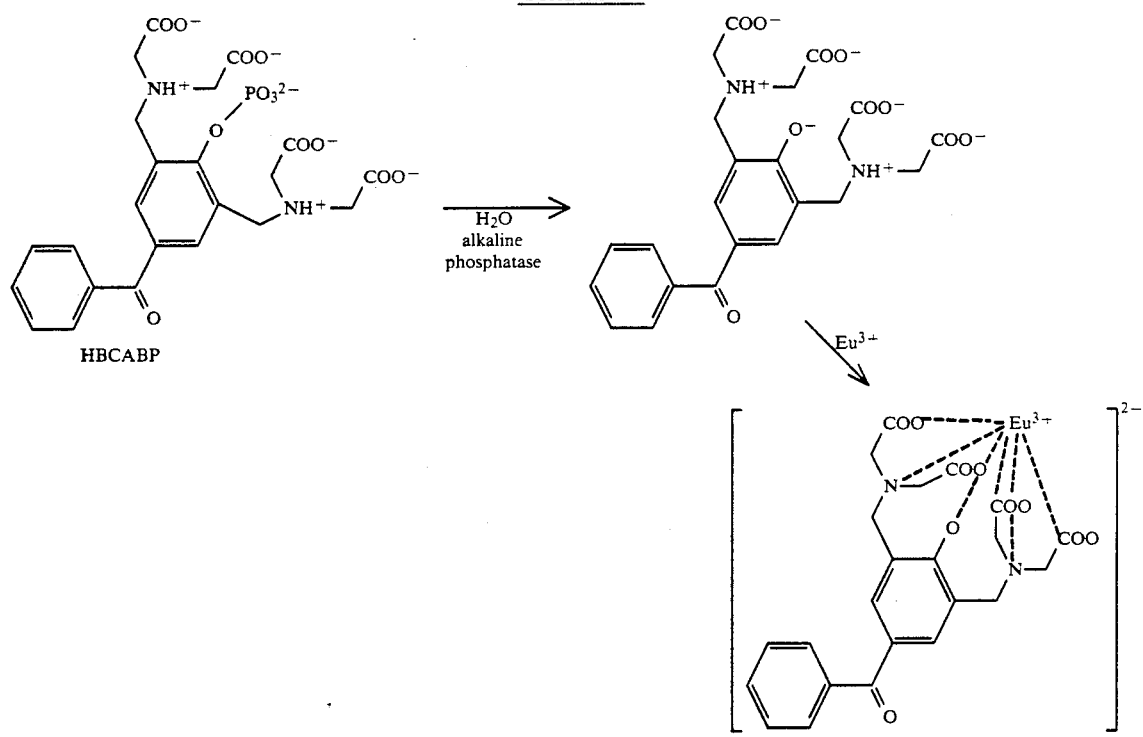

Figure 4:
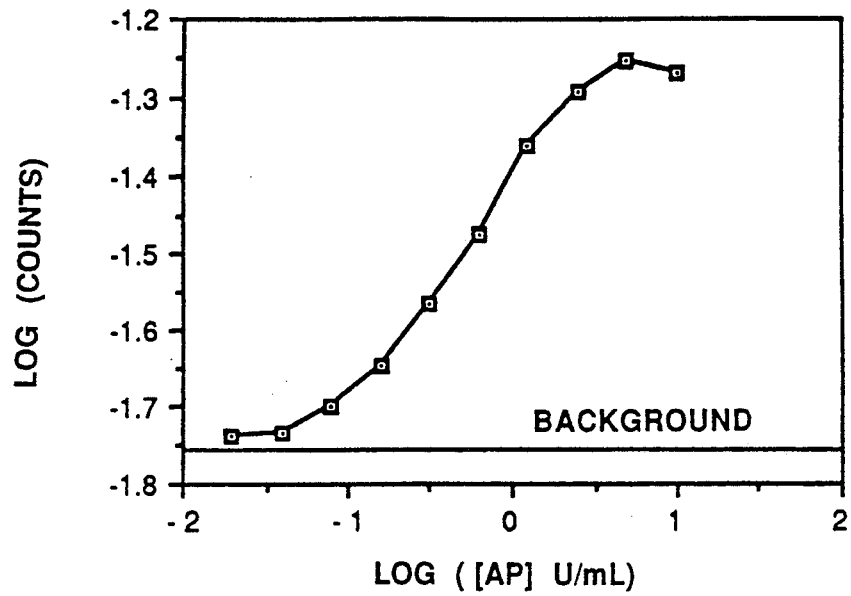
FIG. 4 illustrates the determination of alkaline phosphatase using HBCABP as substrate, as observed by the formation of luminescent Eu:HBCAB complexes.

The UV spectrum of HBCABP in 0.1M Tris pH 8.5 showed a maximum at 268 nm ($\epsilon$=15,340 M$^{-1}$cm$^{-1}$) and no significant absorbance above 310 nm. Addition of alkaline phosphatase (AP, from calf intestine, Boehringer Mannheim, EC 3.1.3.1) to the solution in the absence of heavy metal ions caused gradual transformation to the spectrum of the dephosphorylated product 4-hydroxy-3,5-bis[N,N-bis(carboxymethyl)aminomethyl]benzophenone (HBCAB) with $\lambda_{max}$ at 254 nm and 341 nm. However, it was found that heavy metal ions such as Eu$^{+3}$ and Mg$^{+2}$ at concentrations of 10 $\mu$M and and a time window of 2 ms. A plot of the luminescence counts vs. enzyme concentration (FIG. 4) demonstrates the principle of alkaline phosphatase amplified dephosphorylation of the ligand, which subsequently forms a luminescent europium chelate, with a detection limit of approximately 0.05 units/mL.

EXAMPLE 6. ACETYLSALICYLIC ACID: ESTERASE SUBSTRATE

Figure 5A:
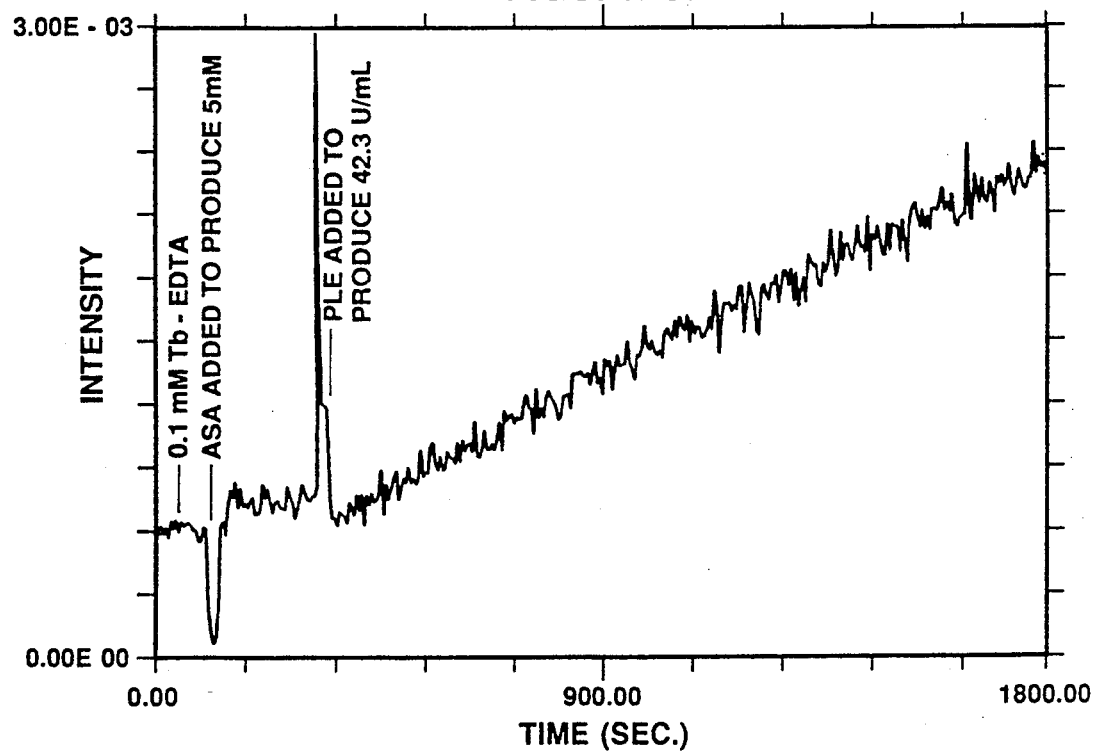
FIGS. 5a and 5b illustrate the production of Tb:salicylic acid:EDTA complexes by the action of esterase on acetylsalicylic acid (ASA) in the presence of Tb and EDTA, as observed by the increase in Tb luminescence upon addition of PLE, a) in 0.1M Tris buffer pH 8.0 and b) in 0.1M borate buffer pH 9.0.
Figure 5B:
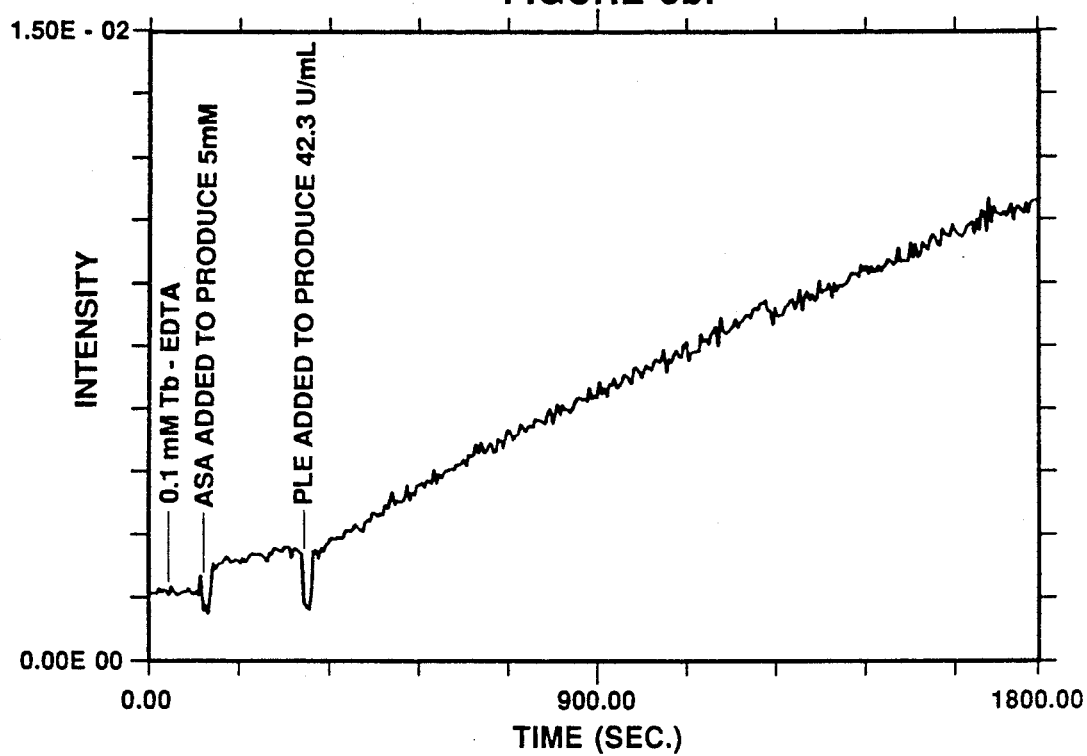

To a solution containing $10^{-4}$ M TbCl$_3$ and $10^{-4}$ M ethylenediaminetetracetate disodium salt (EDTA) in 0.1M Tris buffer pH 8.5 or 0.1M borate buffer pH 9.0 was added acetylsalicylic acid (ASA), to produce an initial ASA concentration of 5 mM. The time-resolved luminescence of the solution in a quartz cuvette was monitored on a SPEX® Fluorolog 212 Spectrofluorometer (SPEX Industries, Inc., Edison, N.J.) using front-face pulsed excitation with the excitation and emission monochromators set at 320 nm and 547 nm, respectively, in the phosphorescence mode with a time delay of 200 μs and a time window of 2 ms. The luminescence intensity was negligible before addition of enzyme but increased gradually after addition of 127 units of pig liver esterase (PLE, EC 3.1.1.1) (Sigma) to 3 mL of the ASA-Tb-EDTA solution (FIG. 5). The generation of the luminescence signal is due to the esterase-catalyzed hydrolysis of ASA and the subsequent instantaneous formation of the 1:1:1 Tb-salicylate-EDTA complex, as illustrated below. Luminescence increase was negligible in a comparable sample without enzyme.

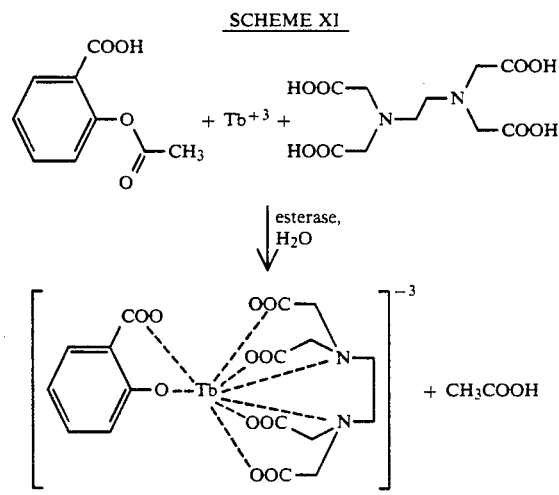

SCHEME XI

EXAMPLE 7. 1,10-PHENANTHROLINE-2,9-DICARBOXYLIC ACID DIHYDRAZIDE USED IN A COUPLED GLUCOSE OXIDASE DETECTION SYSTEM 1,10-Phenanthroline-2,9-dicarboxylic acid dihydrazide (PDAdh) was synthesized as follows. Dimethyl 1,10-phenanthroline -2,9-dicarboxylate (2,9-bis(methoxycarbonyl)-1,10-phenanthroline). was prepared via a slight modification of the procedure of GR Newkome, GE Kiefer, WE Puckett and T Vreland (J. Org. Chem. (1983) 48 5112-4). A solution of the diester (0.206 g, 0.001 mol) in 20 mL DMF was heated with stirring in a 100° C. oil bath. Addition of hydrazine hydrate (2.96 mL of 85% solution, 0.050 mol) caused the formation of a white precipitate. The mixture was heated with stirring at 100° C. for 2 hrs. After cooling to room temperature, the product was collected by vacuum filtration, washed with cold DMF, and dried in vacuum at 60° C. Mp 318°-325° C. (dec). 500 MHz $^1$H NMR in DMSO-d$_6$: δ4.77 broad singlet (4H), δ8.13 singlet (2H), δ8.39 doublet (2H), δ8.69 doublet (2H), δ10.74 singlet (2H).

IR KBr disk: 3500-3700, 3310, 1715, 1680, 1640, 1550, 1495, 1330, 1295, 875, 680 cm$^{-1}$.

A stock solution of $10^{-3}$ M PDAdh in spectroscopic grade dimethylformamide was prepared. The luminescence intensity of a solution of $1.0 \times 10^{-6}$ M PDAdh, $2 \times 10^{-5}$ M EuCl$_3$, 0.1M acetate buffer pH 6.0 was measured in the SPEX spectrofluorometer, using excitation 320 nm, emission 613 nm, excitation and emission bandwidths 14 and 1.6 nm respectively. This remained constant at approximately 11000 counts indefinitely. When H$_2$O$_2$ was added to make $10^{-4}$ M, an immediate growth in luminescence signal was seen; this increase did not occur in the absence of excitation light. This has been ascribed to photo-assisted oxidation of PDAdh by H$_2$O$_2$, as illustrated in the scheme below (assuming complete reaction of both hydrazide groups):

SCHEME XII

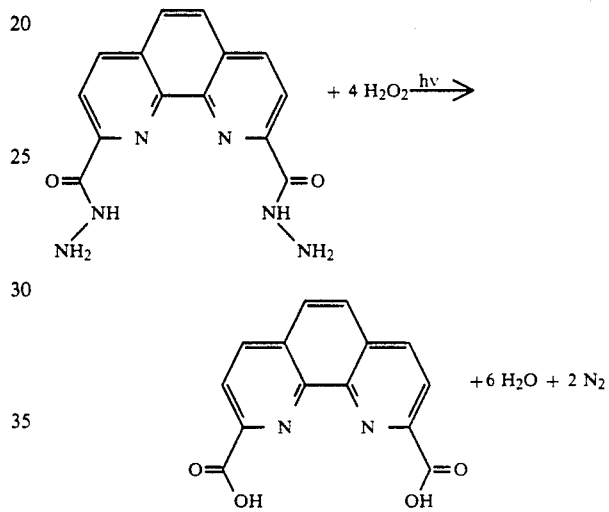

This is followed by formation of Eu:PDA complexes of 1:1 and possible 1:2 stoichiometry as described previously by E Templeton & A Pollak, J. Lumin. 43 (1989) 195-205).

This phenomenon can be used in a coupled system in which β-D-glucose oxidase (GOD EC 1.1.3.4) is detected through the production of H$_2$O$_2$ via the reaction scheme:

SCHEME XIII

β-D-glucose + O$_2$ —GOD→ D-gluconic acid + H$_2$O$_2$ carried out in the presence of PDAdh, Eu, and UV irradiation. PDA:Eu luminescence is only produced in the presence of GOD due to the production of H$_2$O$_2$ and thus this is an example of a coupled system in which the enzyme produces a reagent necessary for subsequent production of a luminescent lanthanide chelate.

Figure 6:
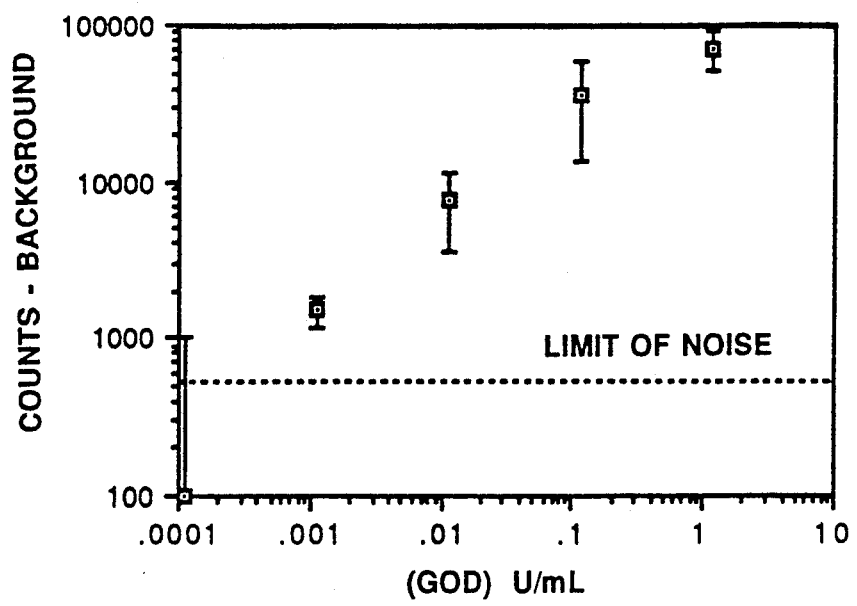
FIG. 6 illustrates the determination of $\beta$-D-glucose oxidase using a coupled system of D-glucose as substrate to produce hydrogen peroxide, followed by photoassisted oxidation of PDAdh by $H_2O_2$ in the presence of Eu, as observed by the formation of luminescent Eu:PDA complexes (stoichiometry 1:1 and/or 1:2)

Ten-fold serial dilutions of GOD (EC 1.1.3.4, Sigma, from *Aspergillus niger*, 1130 U/mL in acetate pH 4) were prepared in triplicate in white microtiter wells (Dynatech, Microlite®) containing 100 μL of 0.1M acetate buffer pH 6.0, 0.01M D-glucose, $1 \times 10^{-5}$ M PDAdh, and $2 \times 10^{-5}$M Eu. Samples containing no GOD were also prepared. These samples were irradiated with a 302 nm UV lamp (Spectroline EB-280C) at a 1 cm distance for 30 minutes. The wells were then read using a CyberFluor 615 Immunoanalyser, which for these samples will measure only Eu luminescence. The results for signal (with background subtracted, as calculated from the sample without GOD; the limit of noise is estimated based on the standard deviation of the background value) are illustrated in FIG. 6, showing a detection limit of less than $10^{-3}$ U of GOD/mL, or $10^{-4}$ U of GOD/well. Note that no signal above background was observed in the absence of UV irradiation.

EXAMPLE 8: DETECTION OF HORSERADISH PEROXIDASE USING TYROSINE-CONTAINING DIPEPTIDES

It is known that many phenols couple in the presence of horseradish peroxidase (HRP, EC1.11.1.7) and $H_2O_2$ to form fluorescent 2,2'-biphenols (GG Guilbault, PJ Brignac and M Juneau, Anal. Chem. (1968) 40: 1256-1263). Such a system is shown here to be suitable for Enzyme Amplified Lanthanide Luminescence (EALL) detection using $Tb^{+3}$ when the phenol to be coupled is a tyrosine containing dipeptide, which contains additional chelating groups. The compounds illustrated in the scheme below are used in the assays for HRP.

The UV-visible spectrum of a 1 mM solution of tyrosine-containing dipeptide (Tyr-Tyr, Tyr-Glu or γ-Glu-Tyr) in 0.1M Tris containing 2 mM $H_2O_2$ showed a $\lambda_{max}$ at 275 nm. Addition of HRP (EC 1.11.1.7, Sigma) to produce an enzyme concentration of 2 U/mL caused the formation of the blue fluorescent dimer with $\lambda_{max}$ around 315 nm.

200 μL solutions containing 1 mM tyrosine-containing dipeptide, 2 mM $H_2O_2$ and two-fold dilutions of HRp from 4.4 unit/mL to 0.018 unit/mL were incubated for 24 hrs at room temperature (24° C.). $TbCl_3$ was added to produce a final $Tb^{+3}$ concentration of 0.5 mM prior to luminescence measurements using the CyberFluor 615 Immunoanalyser.

Figure 7A:
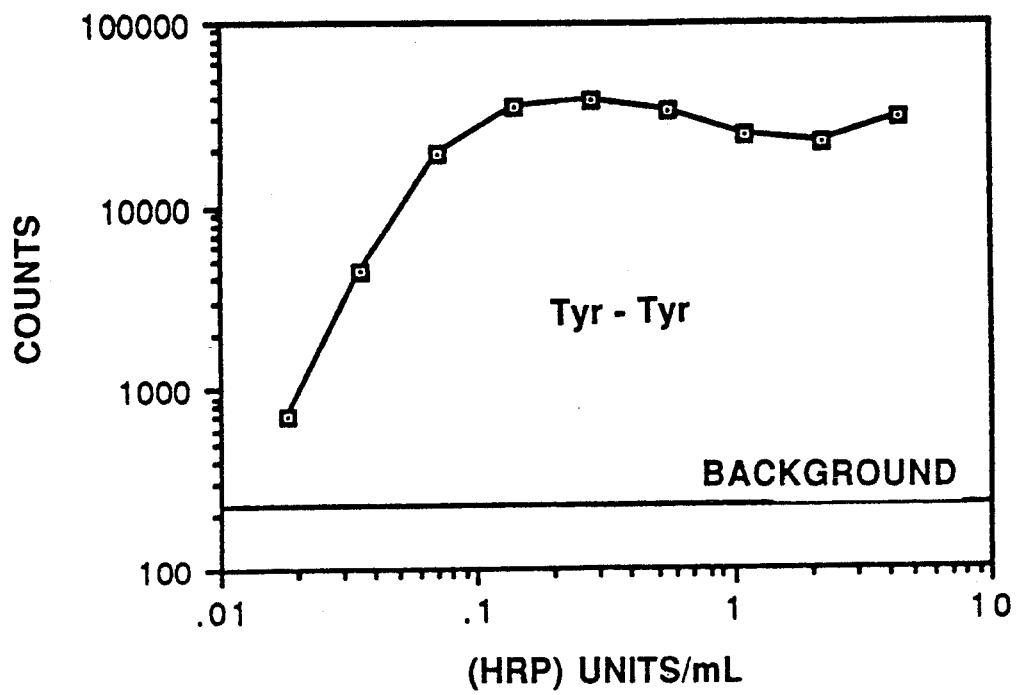
FIGS. 7a, 7b and 7c illustrate the determination of horse-radish peroxidase (HRP) using Tyr-containing dipeptides as observed by the formation of luminescent Tb:coupled dipeptide complexes.
Figure 7B:
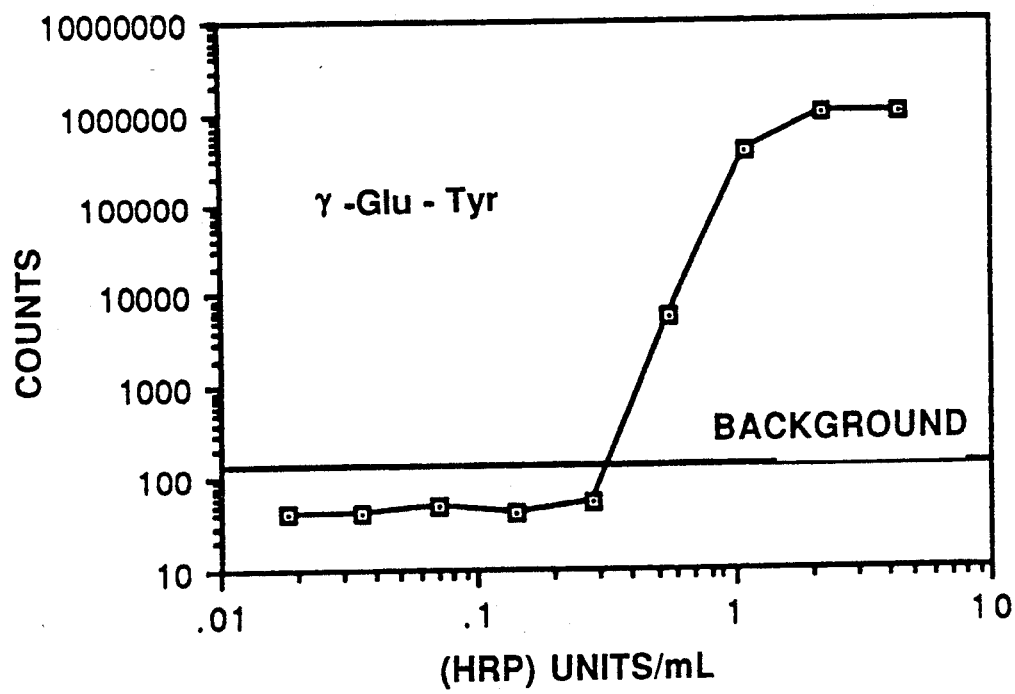
Figure 7C:
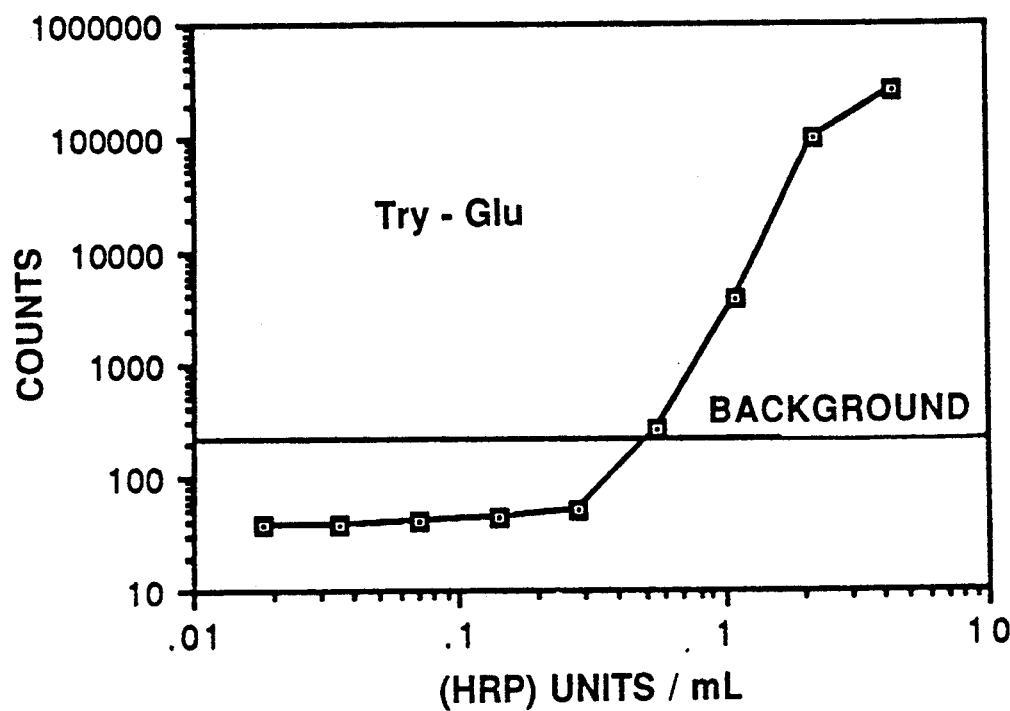

The results show that none of the substrates produce significant Tb luminescence in the presence of $H_2O_2$ without the enzyme and that all are oxidized by the HRP-$H_2O_2$ system to the 2,2'-biphenols which form luminescent Tb chelates (FIG. 7).

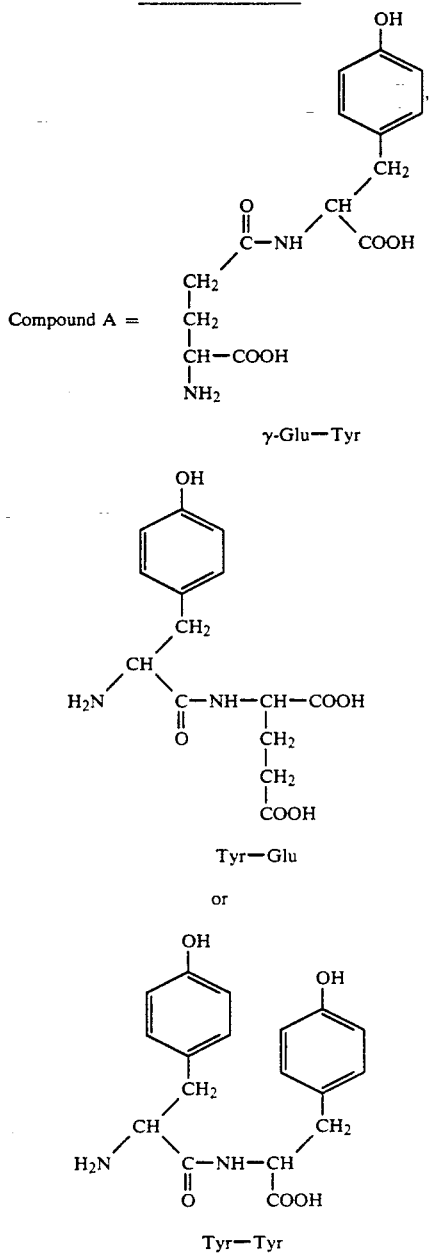

EXAMPLE 9: SUBSTITUTED SALICYL PHOSPHATES: ALKALINE PHOSPHATASE SUBSTRATES

Synthesis

Salicyl phosphate free acids (5-XSAP's) were prepared from the reaction between the salicylic acid (5-XSA: X=H- [Sigma], F- [Aldrich], tert-octyl- [Pfaltz and Bauer], 2',4'-difluorophenyl- (diflusinal, [Sigma])) and phosphorus pentachloride by a modification of the procedure of Chanley et al. (JD Chanley, EM Gindler and H Sobotka, J. Am. Chem. Soc. (1952) 74 4347-52). Salicylic acids were dried in a vacuum oven over KOH pellets prior to reaction. For each reaction, 3-4 g (0.015-0.028 mole) of 5-XSA (X is H, F or tert-octyl) was stirred with the stoichiometric amount of $PCl_5$ in oven-dried glassware fitted with a Drierite drying tube.

Hydrogen chloride gas was liberated and the mixture turned to a clear solution at room temperature in the case of SAP and FSAP and in a 60° oil bath in the case of TOSAP. The mixture was stirred in the bath for 30 min in the case of SAP, 2 hr in the case of FSAP, and 3 hr in the case of TOSAP. The mixture was cooled in an ice bath and then acetone (5-10 mL), toluene (5-10 mL), and water (1-2 mL) were added. After stirring for 30 min at room temperature, more toluene (20 mL) was added. For SAP and FSAP, the white solid free acids precipitated out after a few minutes stirring. The mixture was placed in the freezer to allow more product to precipitate. The products were collected on a sintered glass funnel, dried in vacuum over KOH pellets and recrystallized from acetone-toluene. TOSAP did not precipitate out after addition of toluene so the volatile components were removed on a rotary evaporator. The white solid residue was recrystallized from toluene containing only a very small amount of acetone.

The yields of unpurified products were 59% for SAP, 89% for FSAP and 95% for TOSAP. Each of the salicyl phosphate free acids was recrystallized twice from acetone-toluene. M.p. SAP 160.8°-162° C. (Lit. 162.5°-163° C., Chanley et al.), FSAP 153°-155.5° C., TOSAP 156°-158.5° C. SAP: 400 MHz $^1$H NMR in D$_2$O: $\delta$6.91 (t,1H), $\delta$6.99 (d,1H), $\delta$7.21 (t,1H), $\delta$7.43 (d,1H), $\delta$4.6 (H$_2$O); $-$P NMR in D$_2$O: singlet at $-$4.16 ppm; IR KBr disk: 3300-3600, 2920, 1700, 1610, 1460, 1305, 1220, 1025, 990 cm$^{-1}$. FSAP: 400 MHz $^1$H NMR in D$_2$O: $\delta$6.98-7.02 (m, 2H), $\delta$7.18-7.22 (m, 1H); NMR in D$_2$O: singlet at $-$4.11 ppm; IR KBr disk: 2200-3500, 1710, 1600, 1500, 1460, 1310, 1290, 1200, 1040, 980, 910, 840 cm$^{-1}$. TOSAP: $^1$H NMR in D$_2$O: $\delta$0.36 (s, 9H), $\delta$0.93 (s, 6H), $\delta$1.31 (s, 2H), $\delta$6.98 (d,1H), $\delta$7.16 (d,1H), $\delta$7.51 (s, 1H). $^{31}$P NMR in D$_2$O: singlet at $-$4.76 ppm; IR KBr disk: 2500-3500, 1710, 1590, 1500, 1430, 1320, 1280, 1255, 1230, 1090, 1035, 980 cm$^{-1}$. UV in 0.1M Tris pH 8.5: SAP $\lambda_{max}$=276 nm, $\epsilon$=1570 M$^{-1}$cm$^{-1}$. FSAP $\lambda_{max}$=281 nm, $\epsilon$=2430 M$^{-1}$cm$^{-1}$. TOSAP $\lambda_{max}$=282 nm, $\epsilon$=1850 M$^{-1}$cm$^{-1}$. For diflusinal (DF), a mixture of 3.0 g (12 mmole) of oven-dried DF and 3.0 g (14.4 mmole) of phosphorus pentachloride was heated with stirring in a flask fitted with a Drierite tube for 3 hr at 80° C. The mixture became liquid after evolution of hydrogen chloride gas. With cooling in an ice bath, 5 mL of acetone, 5 mL of toluene and 1.6 mL of water was added. The mixture was stirred at 0° C. for 30 min. Addition of 10 mL toluene and stirring at room temperature for one hour produced a the white solid product which was collected on a sintered glass funnel, washed with toluene-acetone and dried in vacuum. Yield=3.84 g (97%). The product diflusinal phosphate (DFP) was recrystallized twice from acetone-toluene to produce 1.01 g of purified product. Mp 173°-175° C. 400 MHz NMR in (CD$_3$)$_2$SO: $\delta$7.18 (m, 1H), $\delta$7.36, (m, 1H), $\delta$7.48 dd, 1H), 7.59 (m, 1H), $\delta$7.67 (m, 1H), $\delta$7.81 (s, 1H). $^{31}$P NMR in (CD$_3$)$_2$SO: singlet at $-$5.382 ppm relative to H$_3$PO$_4$ in (CD$_3$)$_2$SO. IR KBr disk 2500-3600, 2300 (sh), 1670, 1490, 1220, 1140, 1050, 1040, 980, 850 cm$^{-1}$. $^1$H NMR: UV in 0.1M Tris pH 8.5: $\lambda_{max}$ 250 nm ($\epsilon$=16800 M$^{-1}$cm$^{-1}$) sh 280 nm. DFP has been previously synthesized (Belg. BE 893,563 18 Oct 1982, IT Appl. 81/48,719, 19 Jun 1981, Chem Abst. 98 12563s (1983)).

All of the substituted salicyl phosphates described above show a characteristic red shift in the absorption maximum indicative of conversion to the corresponding salicylic acid in the presence of 1 U of alkaline phosphatase (Ap, EC3.1.3.1, Boehringer Mannheim) in 1 mL of 0.1M tris pH 8.5.

5-Tritylsalicyl phosphate

5-Tritylsalicylic acid phosphate (TRSAP) was prepared as follows. To a warm solution of 5 g (0.0149 mole) vacuum-dried 4-tritylphenol (Aldrich) in 50 mL dry distilled pyridine was added 0.68 g (0.0171 mole) sodium hydroxide pellets. The mixture was heated with stirring under argon in a 100° C. oil bath for 30 min to produce a brown solution. Pyridine was removed by distillation under argon to produce a dark brown liquid residue. More pyridine ($\sim$30 mL) was added and then the volatile components were removed by distillation under argon over a 140° C. oil bath. The remaining volatile components were removed in vacuum with heating at 120° C. to produce the solid sodium 4-tritylphenolate which was further dried in a 80° C. vacuum oven over NaOH pellets.

The beaker containing the dried phenolate salt and a magnetic stirrer was placed in a 473-mL stainless steel Parr reaction bomb model 452HC2. The bomb was charged with carbon dioxide to a pressure of 830 psi, sealed and then heated in a silicone oil bath over a stirrer-hot plate for 8 hr at 180° C. The pressure increased to 1400 psi during the reaction. After cooling to room temperature, excess CO$_2$ was released, the solid was suspended in 100 mL water and then the mixture was acidified to pH 1 by addition of 5M hydrochloric acid. The mixture was alternately sonicated and stirred vigorously to allow protonation of the insoluble sodium 5-tritylsalicylate. The product was collected on a sintered glass funnel, washed with cold water and dried in vacuum. The solid was suspended in 200 mL 5% aqueous NaHCO$_3$ with sonication and stirring to convert the insoluble 5-tritylsalicylic acid to the insoluble sodium 5-tritylsalicylate while keeping the contaminating 4-tritylphenol unconverted. The solid was collected on a sintered glass funnel, washed with water and dried in vacuum. The product was suspended in 150 mL toluene with stirring and sonication to extract the contaminating phenol. The product was collected on a sintered glass funnel and dried in vacuum. The product was acidified to the salicylic acid by suspending the solid with vigorous stirring and sonication in 150 mL 0.5M hydrochloric acid. TLC of the vacuum-dried product still showed presence of 4-tritylphenol, thus the bicarbonate, toluene, and hydrochloric acid treatment was repeated. The dried product was recrystallized from toluene-acetone to produce 2.1 g (37% yield) of pure 5-tritylsalicylic acid (needles). Mp 234°-237° C. NMR in CDCl$_3$$\delta$6.80 (d, 1H), $\delta$6.90 (s, 1H), $\delta$7.3 (s, 15H), $\delta$7.8 (d, 1H). IR KBr disk: 2800-3600, 2600 (sh), 1660, 1610, 1490, 1440, 1300, 1200, 750, 700 cm$^{-1}$.

A mixture of 1.9 g (5 mmole) 5-tritylsalicylic acid and 1.2 g (5.8 mmole) phosphorus pentachloride in 5 mL dry toluene was heated with stirring in a flask fitted with a Drierite tube in an oil bath at 60° C. Hydrogen chloride gas was liberated and the mixture became a clear solution within 3 min. The reaction was allowed to proceed for 3 hr. After cooling to room temperature and then in an ice bath, 1.8 mL acetone and 0.55 mL water were added. The white solid product precipitated out after stirring for 30 min in the ice bath and 1.5 hr at room temperature. After cooling at $-$20° C. to allow more product to precipitate out, the solid was collected on a sintered glass funnel, washed with cold toluene-hexane, and dried in vacuum over KOH pellets. Yield 1.75 g (76%). The product was recrystallized twice from about 250 mL acetone to produce pure 5-tritylsalicyl phosphate (needles). Mp. 197°–199° C. 400MHz $^1$H NMR in $(CD_3)_2SO$: δ7.14 (m, 6H), δ7.205 (tt, 3H), δ7.305 (m, 8H), δ7.55 (d,1H). $^{31}$P NMR in $(CD_3)_2SO$: singlet at −5.398 ppm relative to $H_3PO_4$ in $(CD_3)_2SO$. IR KBr disk 2400–3600, 1690, 1605, 1490, 1230, 1030, 965, 745, 700 cm:

A 0.01M stock solution of TRSAP in 0.1M NaOH Was prepared prior to UV and luminescence measurements. The UV spectrum of 1 mL solution of 0.1 mM TRSAP in 0.1M tris pH 8.5 showed a maximum at 285 nm ($\epsilon = 1500$ M$^{-1}$cm$^{-1}$). Addition of 1 unit of AP to the solution produced a time-dependent transformation to the spectrum of 5-tritylsalicylate with $\lambda_{max}$ at 306 nm with an increase in extinction coefficient. After 20 min of incubation with the enzyme, a white precipitate of 5-tritylsalicylate was formed.

5-Phenylsalicyl Phosphate

A mixture of vacuum-dried 4-phenylphenol (Aldrich) (5.2 g, 3.06 mmole) and sodium hydroxide pellets (1.4 g, 3.5 mmole) in 50 mL dry distilled pyridine was refluxed for 30 min under argon to produce a yellow solution. The volatile components were removed by distillation under argon. More pyridine (50 mL) was added to the residue and the volatiles were again removed by distillation. The yellow solid sodium 4-phenylphenolate was transferred to a 15o mL lipless beaker and then dried in a 180° C. oven for 3 hr. The beaker containing the phenolate salt and a magnetic stirrer were placed in a stainless steel Parr reaction bomb model 452HC2. The bomb was charged with 830 psi carbon dioxide, sealed, and heated in a 160° C. silicone oil bath over a hot plate-stirrer for 8 hrs. The pressure during the reaction was 1300 psi. After cooling to room temperature, $CO_2$ was released and the solid contents were suspended in 120 ml water. Hydrochloric acid was added to acidify the mixture to pH 1 and then the suspension was stirred vigorously and sonicated to allow conversion of the sodium salt to the insoluble 5-phenylsalicylic acid. The product was collected on a sintered glass funnel and dried in vacuum. The solid was suspended in 300 mL 5% aqueous $NaHCO_3$ with vigorous stirring. The contaminating starting material was removed by two extractions with 150-mL portions of toluene. The solid which did not dissolve in either layer was collected with the aqueous layer. The aqueous suspension was acidified to pH 1 by addition of 5N hydrochloric acid and then the product was extracted into two 150-mL portions of ether. Drying over anhydrous $Na_2SO_4$ and concentration in vacuo produced 3.33 g (51%) of 5-phenylsalicylic acid. The product was recrystallized twice from toluene-acetone-heptane to produce needles. Mp 214°–216° C. $^1$H NMR in $CDCl_3$—$(CD_3)_2CO$: δ7.0 (d, 1H), δ7.3–7.8 (m, 6H), δ8.1 d,1H). IR KBr disk 2800–3300, 2600 (sh), 1665, 1610, 1590, 1480, 1450, 1300, 1375, 1335, 1210, 790, 760, 670 cm$^{-1}$.

A mixture of 0.64 q (3 mmole) recrystallized 5-phenylsalicylic acid and 0.72 g (3.45 mmole) phosphorus pentachloride was heated with stirring in a 60° C. oil bath in a flask fitted with a Drierite tube. Hydrogen chloride gas was liberated and the mixture became a liquid after a few minutes stirring. The reaction was allowed to proceed for 3 hr. The reaction mixture was cooled in an ice bath and then 1.5 mL acetone, 1.5 mL toluene and 0.4 mL water was added. The mixture was stirred for 30 min at 0° C. and then at room temperature for 1 hr. The product, 5-phenylsalicyl phosphate (PSAP), was collected on a sintered glass funnel, washed with toluene and dried in vacuum over KOH pellets. Yield 0.67 g (76%). The product was recrystallized twice from toluene-acetone. Mp 174°–175° C. 400 MHz NMR in $(CD_3)_2SO$: δ7.38 (t,1H), δ7.46 (m, 3H), δ7.66 (d, 2H), δ7.81 (dd, 1H), δ7.91 (s, 1H). $^{31}$P NMR in $(CD_3)_2SO$: singlet at −5.129 ppm relative to $H_3PO_4$. UV in 0.1M tris pH 8.5: $\lambda_{max} = 260$ nm ($\epsilon = 25800$ M$^{-1}$cm$^{-1}$).

Addition of 1 unit AP to a 1 mL solution of 50 μM PSAP in 0.1M tris pH 8.5 produced an absorbance decrease in the 260 nm peak leading to the formation of 5-phenylsalicylate with $\lambda_{max}$ at 262 nm and 314 nm.

5-n-Dodecylsalicyl Phosphate

The preparation of 5-n-dodecysalicyl phosphate (NDSAP) involved carboxylation of 4-n-dodecylphenol via the Kolbe-Schmitt reaction followed by phosphorylation with phosphorus pentachloride. A mixture of 4-n-dodecylphenol (Pfaltz and Bauer) (2.62 g, 10 mmole) and sodium hydroxide pellets (0.50 g, 12.5 mmole) in 40 mL dry distilled pyridine was refluxed for 30 min under argon. The resulting solution was concentrated in vacuo to produce a light yellow solid residue which was dried in a vacuum oven at 60° C. over NaOH pellets. The sodium phenolate salt was transferred to a 50 mL glass bottle and dried further in the vacuum oven. The bottle containing the phenolate salt, a magnetic stirrer, and 8 g of dry ice were placed in a 118-mL stainless steel Parr reaction bomb model 425HC. The bomb was sealed and heated in a 130° oil bath over a hot plate stirrer for 6 hr. The pressure during the reaction was expected to be about 50 atm assuming $CO_2$ behaves as an ideal gas. The bomb was cooled in dry ice and then opened cautiously. The contents were dissolved in 30 mL water and then acidified to pH 1 by addition of 5 N hydrochloric acid. The sticky solid precipitate was isolated and dried in vacuum over KOH pellets. The solid was suspended with vigorous stirring in 100 mL 5% aqueous $NaHCO_3$ to convert the 5-n-dodecylsalicylic acid to the salicylate salt and keep the contaminating phenol unconverted. The phenol was removed by extraction with toluene. The layers separated very slowly due to stabilization of the emulsion by the detergent-like product. The aqueous layer was acidified to pH 1 by addition of hydrochloric acid and then the product was extracted with ether. Removal of volatiles in vacuo produced a viscous liquid which was shown to be about 95% pure by TLC on silica using 70% hexane-30% ethyl acetate as eluting solvent.

A mixture of 5-n-dodecylsalicylic acid (0.65 g, 2.1 mmole) and phosphorus pentachloride (0.49 g, 2.4 mmole) was heated with stirring in an oil bath at 80° C. for 3 hr under a Drierite tube. The mixture became liquid after evolution of hydrogen chloride gas. While cooling in an ice bath, 1 mL acetone, 1 mL toluene and 0.3 mL water was added. The mixture was stirred at 0° C. for 30 min and at room temperature for 1 hr. The volatile components were removed in vacuo to produce a solid residue which was recrystallized from hexane-toluene. Yield 390 mg (47%). Three more recrystallizations from hexane-toluene produced 100 mg of purified NDSAP. Mp 114°–116° C. 400 MHz NMR in $(CD_3)_2SO$: δ0.6–1.8 (m, 25H), δ7.38 (m,1H), δ7.59 (m, 1H), δ7.87 (m, 1H), δ10.14 (bs, 3H). $^{31}$P NMR in $(CD_3)_2CO$: singlet at −2.581 relative to $H_3PO_4$. IR KBr disk: 2500–3500, 2300 (sh), 1700, 1600, 1580, 1490, 1230, 1080, 1020, 970, 830 cm$^{-1}$. UV in 0.1M tris pH 8.5: $\lambda_{max}$=281 nm ($\epsilon$=1740 cm$^{-1}$). Addition of 2 units Ap to 1 mL 0.2 mM NDSAP in 0.1M tris pH 8.5 produced a gradual conversion to the spectrum of 5-n-dodecylsalicylate with $\lambda_{max}$ at 303 nm.

5-Methylsalicyl Phosphate and 4-Diethylaminosalicyl Phosphate

5-Methylsalicyl phosphate (MSAP) was prepared from 5-methylsalicylic acid (Aldrich) and 4-diethylaminosalicyl phosphate (DEASAP) was prepared from 4-diethylaminosalicylic acid (Pfaltz and Bauer) by phosphorylation of the corresponding methyl salicylate with an equimolar amount of phosphorus oxychloride in pyridine at 0° C. followed by hydrolysis of the methyl ester at pH 12-13 at room temperature. MSAP and DEASAP trisodium salts were purified by anion exchange chromatography through a Pharmacia Mono Q column using a linear (0.2→1M) gradient of NaCl containing 0.01M NaOH with UV monitoring at 254 nm.

Addition of 1 unit AP to a solution of MSAP ($\lambda_{max}$=282 nm) in 0.1M tris pH 8.5 caused the gradual formation of 5-methylsalicylate ($\lambda_{max}$=305 nm). MSAP has been previously synthesized (M. M. Tessler, Fr. Demande 2,132,674, Dec. 29, 1972, U.S. application No. 132,167, Apr. 7, 1971, Chem. Abst. 79 7134m (1973); R. H. Bromilow and A. J. Kirby, J. Chem. Soc. Perkin Trans. 2, 149-55 (1972)).

EXAMPLE 10: DETECTION OF AP USING SAP'S IN HOMOGENEOUS ASSAY

The generalized reaction for alkaline phosphatase-catalyzed dephosphorylation of 5-substituted salicylic acids is illustrated in the scheme below:

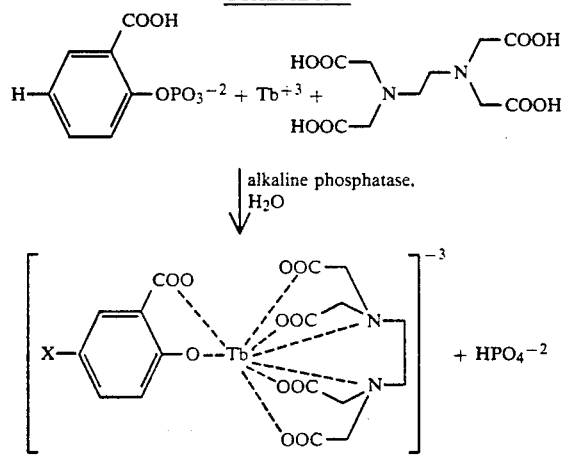

SCHEME XV

Figure 8:
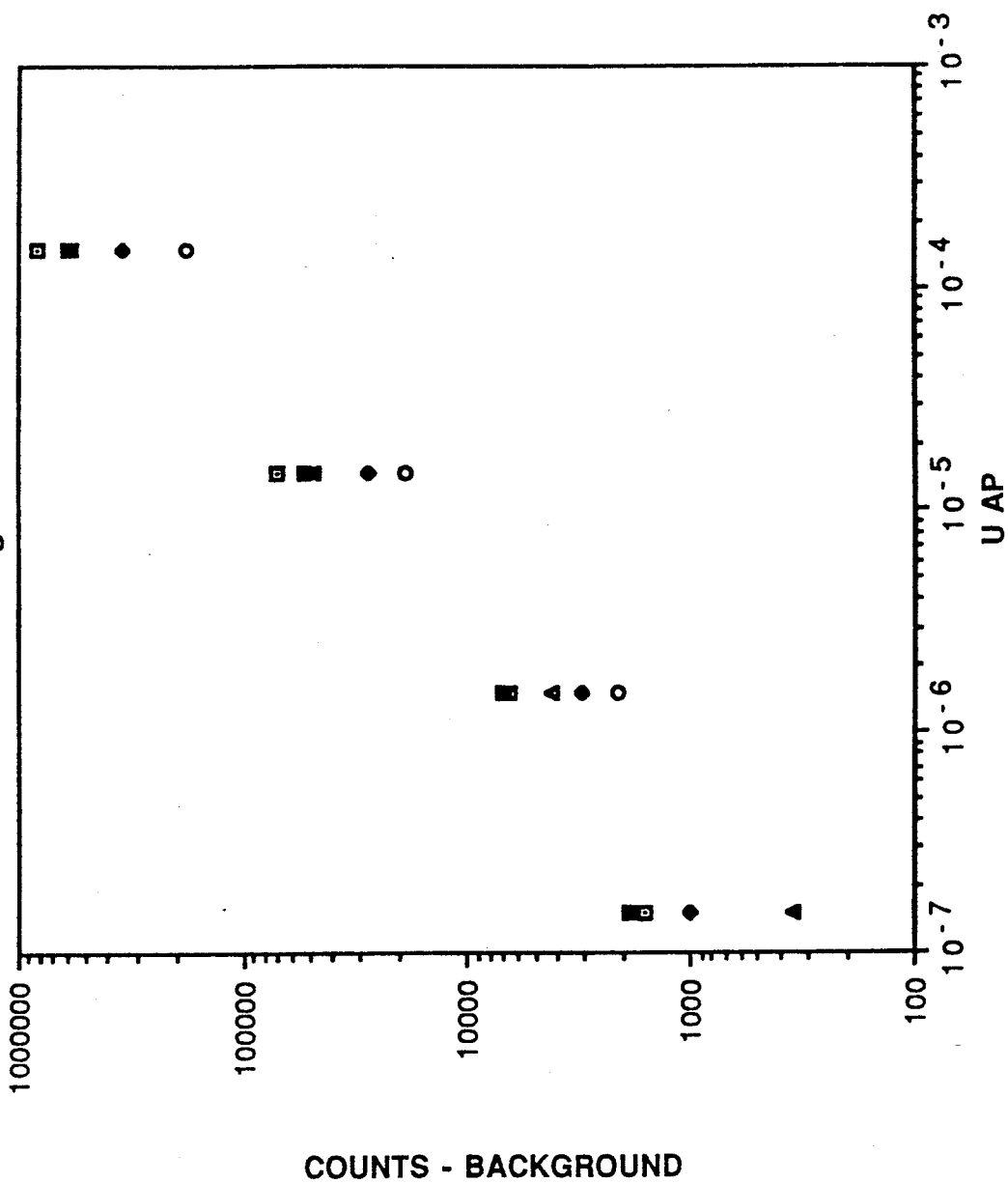
FIG. 8 illustrates the determination of alkaline phosphatase (AP) in homogeneous solution phase assay using substituted salicyl phosphates, as detected by the luminescence of the Tb:substituted SA:EDTA complex.

The detection of AP in solution was demonstrated with the following salicyl phosphate derivatives: X=F, tert-octyl, phenyl, trityl and 2',4'-difluorophenyl. Serial dilutions of AP (Calf intestine, Boehringer Mannheim) of concentration 10$^{-4}$, 10$^{-5}$, 10$^{-6}$, 10$^{-7}$, 10$^{-8}$ U/10 $\mu$L were prepared in T9 buffer (0.1M tris pH 9.0, 0.1M NaCl). Samples consisting of 15 $\mu$L of each enzyme dilution and 135 $\mu$L of 10$^{-3}$ M of substrate in T9 buffer (except for TRSAP which due to limited solubility at pH 9.0 was used in 0.1M 2-amino-2-methyl-1-propanol buffer, pH 9.6) were prepared in microtiter wells (Microlite Removawell™, Dynatech). In addition, MgCl$_2$ was present either in the enzyme dilutions or the substrate solution to give a concentration of 1×10$^{-5}$ M in the final samples. The samples were allowed to incubate at room temperature for 1 hour. The signal was developed by the addition of 150 $\mu$L of a freshly prepared solution of 5×10$^{-3}$ M TbCl$_3$, 5×10$^{-3}$ M disodium EDTA in 0.32M NaOH. The wells were read on the CyberFluor 615 Immunoanalyser plate reader. The results are shown (with background, calculated from sample containing 1.5×10$^{-8}$ U AP, subtracted) in FIG. 8 indicating detectability of about 10$^{-6}$ U of AP in 1 hour.

EXAMPLE 11. DETECTION OF BIOTINYLATED-BSA USING SALICYL PHOSPHATE/ALKALINE PHOSPHATASE-LABELED AVIDIN DETECTION SYSTEM

Figure 9:
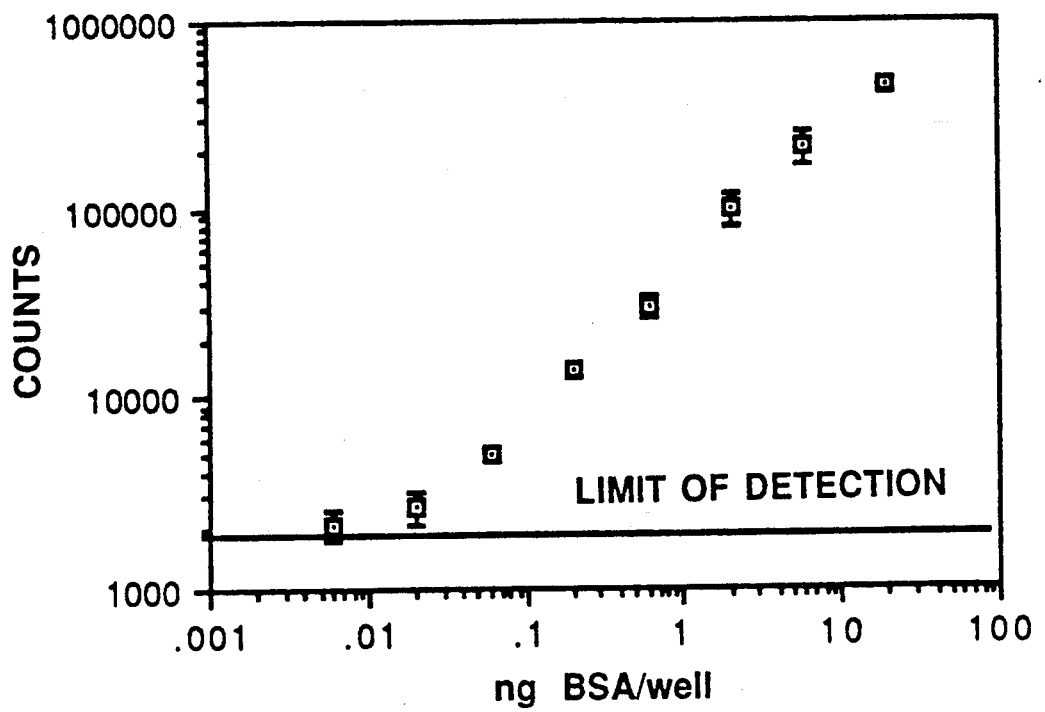
FIG. 9 illustrates the quantitation of biotinylated bovine serum albumin (BSA) immobilized in microwells, by subsequent binding with avidin-AP, and detecting the AP using SAP as substrate Luminescence signal from the Tb:SA:EDTA complex, which was formed upon addition of $Tb^{3+}$ and EDTA after enzymatic reaction had proceeded for 30 minutes, was measured on the CyberFluor 615 Immunoanalyser.

This detection system was used in a heterogeneous assay for biotinylated bovine serum albumin (Bio-BSA, Sigma, 10.7 mol biotin/mol BSA). The Bio-BSA was prepared by serial dilution into coating buffer (0.05M carbonate buffer pH 9.5), from a stock solution of 2 $\mu$g/mL in the same buffer, to give 1 mL samples of concentrations 200, 60, 20, 6, 2, 0.6, 0.2, 0.06 ng/mL. 100 $\mu$L of each of these solutions was dispensed into white microtiter wells in triplicate (Dynatech Microlite Removawell strips), and left at 4° C. for 48 hr to coat. The wells were then aspirated, and washed twice with the coating buffer (all washing was done with a SLT EAWII automatic washer). Avidin conjugated to alkaline phosphatase (Av-AP, Sigma, 3.8 avidin units/mg protein, 390 AP units/mg protein, 1.4 mol AP/mol avidin) was used to detect the Bio-BSA; 100 $\mu$L solution of 0.02 $\mu$g/mL Av-AP in assay buffer (0.01 mol/L Tris buffer pH 8.5, 3% KCl, 10% BSA, 0.05% sodium azide) was added to each well and allowed to react for 1 hr at room temperature with gentle shaking. This solution was aspirated and the wells washed 4× with wash solution (assay buffer+130 $\mu$L/L Tween 20 detergent). To each well was added 100 $\mu$L of 1×10$^{-4}$ M SAP in 0.01M borate buffer pH 10.0, and enzymatic reaction was allowed to proceed 30 minutes at room temperature with gentle shaking. To develop the signal and stop the enzymatic reaction, to each well was added 30 $\mu$L of a solution of 3.3×10$^{-4}$ M TbCl$_3$, 3.3×10$^{-4}$ M Na$_2$EDTA, 0.33M NaOH (without aspirating the previous solution). The wells were then read on a CyberFluor 615 plate reader. The results are illustrated in FIG. 9, with mean luminescence counts and standard deviation of the three readings plotted vs amount of Bio-BSA added to each well. No background signal has been subtracted, and the detection limit is estimated as a reading 2 standard deviations from the background. These results show a detection limit of approximately 0.03 ng Bio-BSA/well.

EXAMPLE 12: DNA HYBRIDIZATION ASSAY IN MICROWELL FORMAT FOR pBR322 DETECTED USING FSAP AND BCAHAP

The alkaline phosphatase substrate 2-[N,N-bis(carboxymethyl)amino]acetophenone-4'- phosphate (BCAHAP) was synthesized as illustrated in the scheme below:

SCHEME XVI

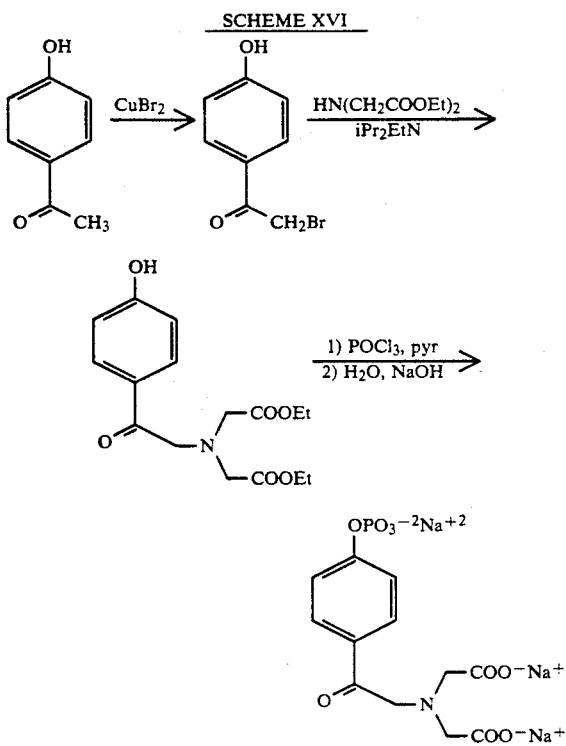

2-Bromo-4'-hydroxyacetophenone was prepared by bromination of 4-hydroxyacetophenone with copper (II) bromide using the procedure of Malik and Grover (Indian J. Chem. (1976) 14B: 513–515) and was purified by flash chromatography through a silica column using 70% hexane-30% ethyl acetate as eluting solvent and then recrystallized from hexane-ethyl acetate.

To a stirred solution of diethyl iminodiacetate (0.34 g, 1.8 mmole) and distilled diisopropylethylamine (0.23 g, 1.8 mmole) in 5 mL distilled acetonitrile was added via a cannula a solution of 2-bromo-4'-hydroxyacetophenone (0.32 g, 1.5 mmole) in 5 mL acetonitrile. The mixture was heated with stirring in an oil bath at 90° C. under nitrogen for 3 hrs. After cooling to room temperature, the volatile components were removed in vacuo. The product was extracted with ethyl acetate and washed with pH 6.9 aqueous buffer composed of dissolved $CO_2$ and sodium bicarbonate. After separation of layers, a small amount of ethanol was added to the organic layer to dissolve some suspended solid. Drying over sodium sulfate, concentration in vacuo and flash chromatography through a silica column using 55% hexane-45% ethyl acetate produced 194 mg (40% yield) of 2-[N,N-bis(carboxymethyl)amino]-4'-hydroxyacetophenone diethyl ester (BCAHA diethyl ester), a waxy solid with $R_f$=0.44. IR 3200–3500, 2900–3000, 1740, 1680, 1610, 1580, 1200, 1030, 990, 850 cm$^{-1}$. 400 MHz $^1$H NMR in $CDCl_3$ $\delta$1.24 (t, 6H), $\delta$3.70 (s, 4H), $\delta$4.15 (q, 4H), $\delta$4.29 (s, 2H), $\delta$6.82-7.84 (A$_2$B$_2$ pattern, 4H), $\delta$7.24 (s, 1H).

To a stirred solution of 129 mg (0.4 mmole) BCAHA diethyl ester in 4 mL distilled pyridine under nitrogen in an ice bath was added 45 $\mu$L (0.48 mmole) distilled phosphorus oxychloride. The reaction was allowed to proceed for two hrs at 0° C. and then the mixture was stirred at room temperature for two hours. The mixture was again cooled in an ice bath and then 4 mL of water was added to destroy the phosphorochloridate groups. Aqueous NaOH solution was added to hydrolyze the ethyl ester groups and maintain the pH between 12 and 13. After more than an hour of stirring and slow addition of NaOH, the volatile components were removed by vacuum evaporation and then the solid residue of crude BCAHAP was dried in high vacuum. The IR spectrum showed the carboxylate salt peak at 1600 cm$^{-1}$ and no ester carbonyl above 1700 cm$^{-1}$.

BCAHAP tetrasodium salt was purified by anion exchange chromatography through the Pharmacia FPLC Mono Q column using a linear NaCl gradient (0→1M) with 0.01M NaOH at a flow rate of 0.5 mL/min. The product which eluted at 0.26M NaCl was the largest of four major fractions. To obtain a purer sample, a second chromatography was performed after five days using an NaCl gradient of 0.1→0.5M under the same conditions as the first purification. The chromatogram consisted of essentially a single peak which eluted at 0.28M NaCl. The purified BCAHAP tetrasodium salt was stored in 0.04M HEPES buffer pH 7.0 at 4° C. The UV spectrum of a solution composed of 12 $\mu$M BCAHAP and 10 $\mu$M $EuCl_3$ in 0.1M carbonate pH 10 showed a $\lambda_{max}$ at 270 nm. Addition of AP to produce an enzyme concentration of 1 U/mL produced a time-dependent transformation to the spectrum of the luminescent Eu-BCAHA chelate with $\lambda_{max}$ at 330 nm. This substrate illustrates enzyme amplification of lanthanide luminescence wherein the chelating group remains unchanged during the enzymatic reaction. The generation of luminescence is due solely to a change in the spectroscopy of the chromophore.

Figure 10A:
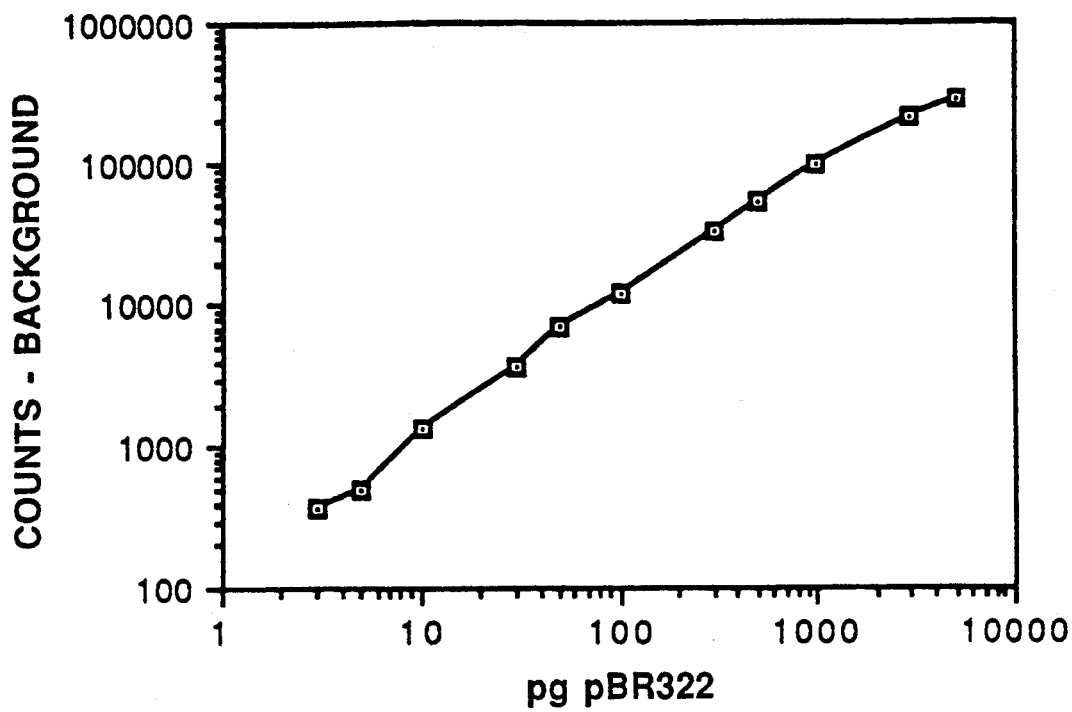
FIGS. 10a and 10b illustrate a pBR322 hybridization assay in microwells, detected using biotinylated pBR322 probe, subsequent binding with avidin-AP, and using a) BCAHAP as substrate, luminescence quantitated of Eu:BCAHA complex, and b) FSAP as substrate, luminescence quantitated of Tb:FSA:EDTA complex.
Figure 10B:
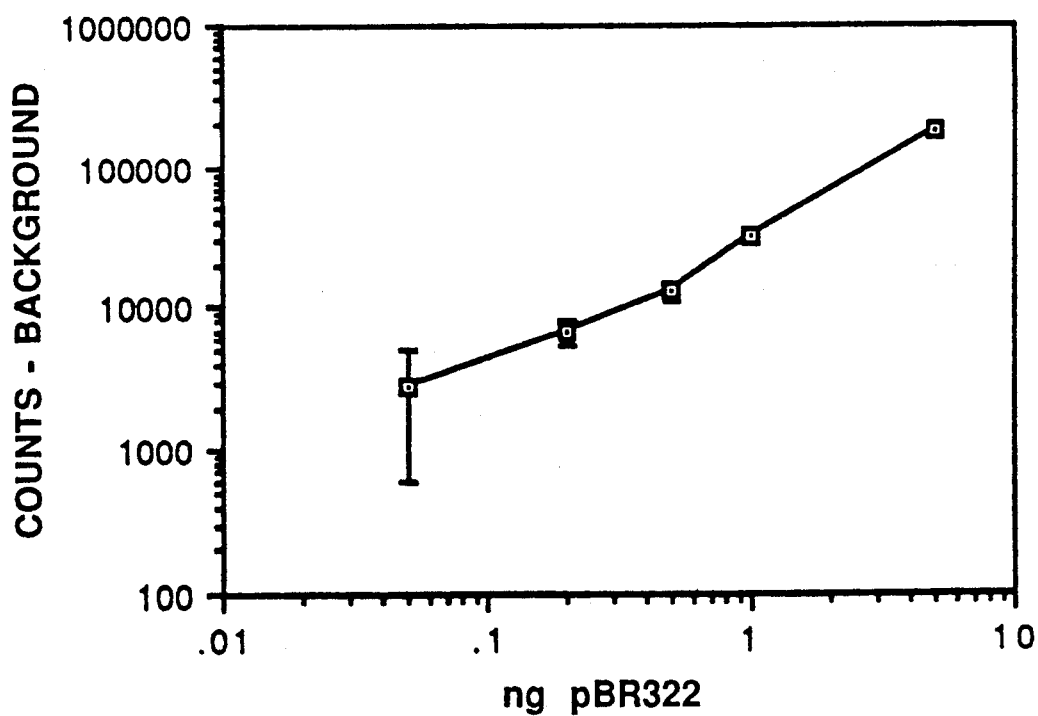

DNA hybridization assays were performed using pBR322 (linearized with Hind III enzyme) as the target sequence, and detected with biotinylated probe and avidin-AP and FSAP or BCAHAP. Each sample containing the desired amount of the target DNA sequence was denatured at 100° C. for 10 minutes in a volume of 25 $\mu$L DNA dilution buffer containing 2 $\mu$g/mL salmon sperm DNA in phosphate buffered saline (10mM phosphate, 140 mM NaCl/KCl, pH 7.2). This volume was then added to a polystyrene microwell (Dynatech Microlite ®) followed by an equal volume of 2× immobilization buffer (phosphate buffered saline containing 0.2M $MgCl_2$. $6H_2O$). The samples were thoroughly agitated, sealed and left to immobilize overnight at room temperature. The wells were then aspirated, allowed to dry, and irradiated using a 254 nm lamp for 6 minutes at 1.6 kJ/m$^2$ to bind the DNA. The wells were prehybridized for 1 hour at 42° C. with 200 $\mu$L prehybridization buffer (6× SSC (1× SSC=0.15M NaCl, 0.015M sodium citrate, pH 7.0), 50% deionized formamide, 5× modified Denhardt's solution (0.2 mg/ml freshly denatured salmon sperm DNA, 1 mg/ml gelatin (Knox), 50 mg/ml polyethylene-glycol, MW 8000) and then aspirated. For hybridization, 100 $\mu$L of pre-hybridization solution containing 50 ng/ml or 125 ng/ml (for BCAHAP and FSAP experiments respectively) of biotinylated probe (Enzo pBR322 BioProbe) was added, the wells were sealed, and incubated overnight at 42° C. The wells were then washed twice with 2X SSC, 0.1% SDS for 5 minutes at room temperature, and twice with 0.1X SSC, 0.1% SDS for 20 minutes at 42° C. to remove nonspecifically bound probe. The wells were then blocked with 5 mg/mL blocking agent from Boehringer Mannheim DNA detection and labelling kit (nonradioactive) in the case of BCAHAP, or 0.5% powdered skim milk in the case of FSAP, both in Buffer 1 (0.1M Tris, 0.15M NaCl, pH 7.5) followed by addition of 500 ng/mL alkaline phosphatase-labeled avidin (Sigma) in Buffer 1. Nonspecifically bound AP was removed by washing 3 times with Buffer 1 for 10 minutes at room temperature with thorough agitation, or using an automatic plate washer (6 times). In one experiment, detection of the AP was performed by addition of 150 μL FSAP solution ($10^{-3}$ M in T9 buffer containing 1 mM $MgCl_2$). The substrate was allowed to incubate for 16 hours and the reaction was terminated by the addition of 150 μL of $5 \times 10^{-3}$ M Tb:EDTA in 0.8M NaOH solution followed by gentle agitation. Signals higher than background were seen down to 3 pg target sequence (FIG. 10a). In another experiment, the substrate BCAHAP ($2.4 \times 10^{-5}$ M in 0.1M carbonate pH 10, $1 \times 10^{-5}$ M $Eu^{+3}$) was allowed to incubate for 2.5 hr and then read on the CyberFluor 615 Immunoanalyser. Signals higher than background were seen down to 50 pg target sequence (FIG. 10b).

EXAMPLE 13. IMMUNOASSAY FOR RAT IgG DETECTED USING SAP

Figure 11:
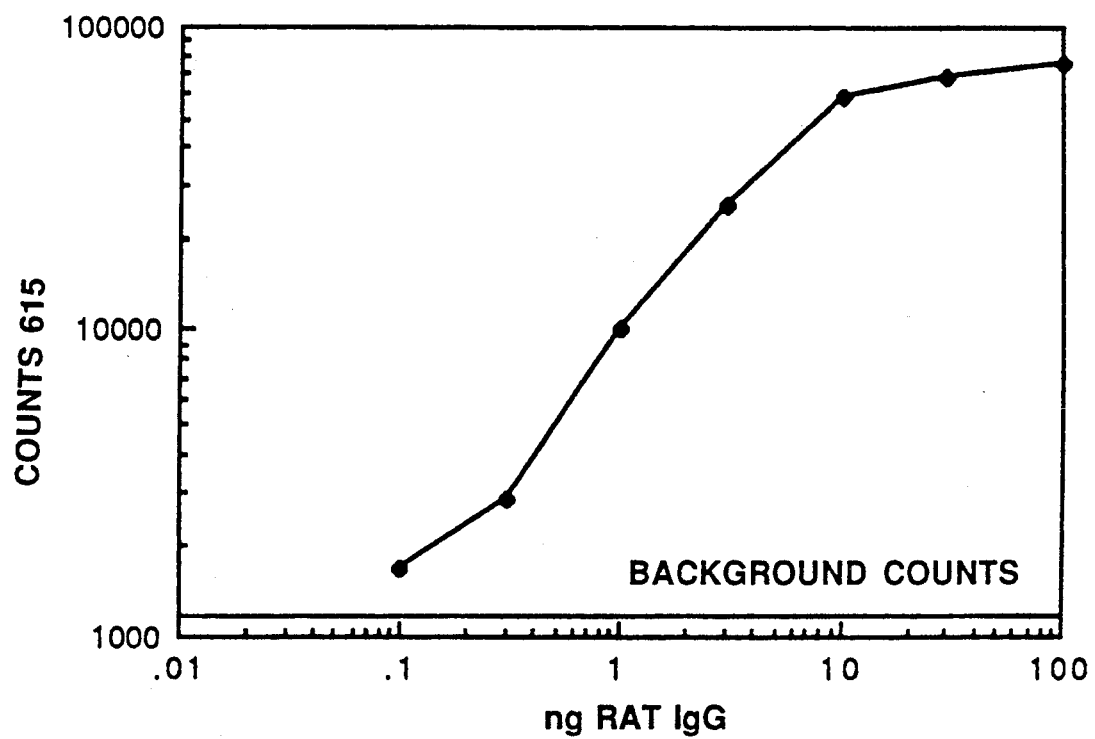
FIG. 11 illustrates the results of a rat IgG sandwich immunoassay, using goat anti-Rat IgG as capture antibody, and alkaline phosphatase-labeled goat anti-Rat IgG with substrate SAP to detect luminescence of Tb:SA:EDTA complex.

A sandwich-type immunoassay for Rat IgG was performed. Dynatech Removawell white wells were coated overnight at 4° C. with 200 ng/well anti-Rat IgG (Sigma, from Goat) in 0.05M carbonate pH 9.6. The wells were washed 2× using the automatic plate washer with wash solution (9 g/L NaCl, 0.5 mL Tween 20/L). Wells were then blocked with 200 μL/well 0.1 mol/L carbonate pH 8.3 containing 10 g/L BSA, 20g/L sucrose. Dilutions of Rat IgG in 10mM phosphate pH 7.0, 10 g/L BSA were prepared to give amounts in the series 100, 30, 10, 3, 1, 0.3, 0.1, 0 ng/well. These were added to the wells in duplicate and left at 42° C. for 1 hr. The wells were aspirated and 100 μL/well AP-anti-Rat IgG solution (Sigma, 0.86 μg/mL in 50 mM Tris pH 7.8, containing 1% BSA, 0.9% NaCl, 0.01% sodium azide; anti-Rat IgG from Goat) was added, for 0.75 hr at 42° C. The wells were washed 2× with wash solution (0.9% NaCl, 0.05% Tween 20) using the automatic plate washer. 100 μL/well of SAP ($10^{-4}$ M in 0.01 borate pH 10) was added and incubated for 10 minutes shaking. 10 μL/well of $5 \times 10^{-3}$ M Tb:EDTA in 0.8M NaOH was added, and the luminescence was read on the CyberFluor 615 Immunoanalyser. Less than 100 pg of Rat IgG was detectable using this method (see FIG. 11)

EXAMPLE 14. DNA DOT-BLOT AND SOUTHERN BLOT HYBRIDIZATION ASSAYS USING TOSAP ON MEMBRANES

Figure 12:
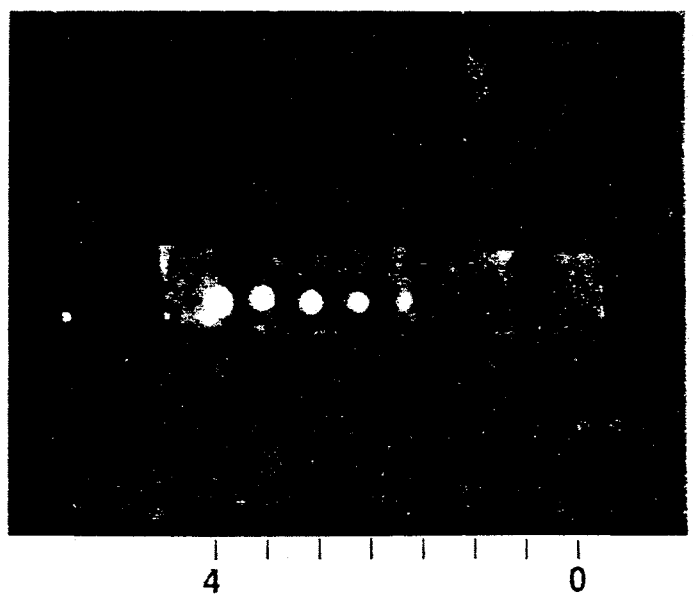
FIG. 12 is a time-resolved photograph of pBR322 dot-blot hybridization assay, detected using biotinylated pBR322 probe, subsequent binding with avidin-AP, with TOSAP as substrate, and luminescence detection of Tb:TOSA:EDTA complex. Spots (from left) contain 4, 1, 0.25, 0.06, 0.016, 0.004, 0.001, 0 ng pBR322.

A dot-blot DNA hybridization assay for linearized pBR322 was performed on nylon membranes as follows. Dilutions of Hind III digested pBR322 were prepared consisting of 4000, 1000, 250, 63, 16, 4, 1, and 0 pg pBR322/2 μL of dilution buffer (PBS pH 7.2 containing 200 ng sheared salmon sperm DNA/2 μL). The DNA was denatured at 100° C. for 10 minutes and placed on ice. pBR322 dilutions (2 μL volumes) were spotted in 6 replicates on nylon membrane (approx. 100 cm² Nytran 0.45 μm, Schleicher & Schuell) and allowed to dry. The membrane was irradiated to immobilize the DNA with 254 nm UV light for 3 minutes. The membrane was prehybridized in a sealed plastic bag for 2 hr at 42° C. in 10 mL prehybridization buffer (6X SSC, 0.1% Ficoll 400, 0.1% polyvinylpyrrolidone, 0.5% powdered skim milk, 50% formamide, 200 μg/mL freshly denatured sheared salmon sperm DNA, 5% polyethylene glycol MW 8000). The prehybridization buffer was removed and 6.0 mL of hybridization buffer (prehybridization buffer containing 100 ng/mL biotinylated nick-translated pBR322 probe, ENZO Bioprobe) added. The membrane was sealed in a plastic bag and hybridized at 42° C. overnight with shaking. The membrane was then washed twice in 100 mL of 5X SSC, 0.5% SDS for 5 minutes at 65° C., once in 100 mL of 0.1X SSC, 1% SDS for 30 minutes at 65° C., and once in 100 ml 2X SSC for 5 minutes at room temperature. The membrane was soaked for 1 minute in TBS-T20 (0.1M tris pH 7.5, 0.1M NaCl, 0.05% Tween 20) and then blocked with 100 mL of 1% BSA in TBS-T20 at 65° C. for 1 hr. The membrane was then incubated with 50 mL of a 1:6000 dilution of streptavidin-alkaline phosphatase (ExtrAvidin ™, Sigma) in TBS-T20 for 10 minutes. The membrane was washed twice with 100 mL of TBS-T20 for 15 minutes and once with 100 mL substrate buffer (0.1M tris 0.1M NaCl $10^{-3}$ M $MgCl_2$ pH 9.0) for 1 hour. The membrane was laid on blotting paper (DNA side up) to remove excess liquid, and cut into 6 sets of strips containing 1 serial dilution each for developing. Strips were incubated 2–4 hours with substrate (0.2 mL of $10^{-3}$ M TOSAP in substrate buffer). Each strip was lightly blotted from behind with blotting paper, and then 0.4 mL developing solution added ($1 \times 10^{-3}$ M Tb:EDTA, 0.32M NaOH). For both of the previous steps the solution added was spread over the membrane, while it was contained in a plastic bag open on three sides, by rolling several times with a 10 mL disposable pipet. The membrane was then photographed in a TRP100 time-resolved photographic camera (Kronem Systems Inc., Mississauga, Canada), using 320 nm cutoff excitation and 515 nm cutoff emission filters, 6000 rpm speed, and 2 minute exposure on Polaroid 612 instant film. Signals above background were observed in the photograph for samples down to 16 pg pBR322 for 2 hour incubation (FIG. 12) and 4 pg for 4 hour incubation with substrate.

A Southern blot assay was performed for linearized and digested pBR322 as follows. Five samples consisting of each of 25, 6.2, 1.6, 0.4 and 0.1 ng of a BstN I enzyme digest of pBR322 DNA in 5 μL of loading buffer (15% Ficoll type 400 in deionized water) and a control sample consisting of 750 ng of Hind III digested λ-DNA in 5 μL of loading buffer were prepared for electrophoresis on a 1.0% agarose gel. The gel was run at 40 volts, 0.04 amperes for 3 hr in 1X TBE buffer (0.089M Tris, 0.089M boric acid, 0.002M EDTA, pH 8.3). The gel was stained in 0.5 μg/mL ethidium bromide in deionized water for 40 minutes and then examined on a 300 nm transilluminator to locate the bands in the control λ-DNA ladder. The transfer of the DNA from the agarose gel to nylon membrane was performed as follows. The DNA was denatured by shaking the gel in denaturing solution (1.5M NaCl, 0.5M NaOH) for 30 minutes at room temperature; this was repeated once. The gel was neutralized by shaking in 1.0M tris pH 8.0, 1.5M NaCl for 30 min at room temperature. The Southern transfer was performed on nylon membrane (Nytran, Schleicher & Schuell) following standard procedure such as those taught by Maniatis et al. (T Maniatis, EF Fritsch, J Sambrook, "Molecular Cloning, A Laboratory Manual", Cold Spring Harbor Laboratory, 1982). The transfer buffer was 10X SSC (1.5M NaCl, 0.15M sodium citrate, pH 7.0) and the transfer was performed for 18 hours using Whatman 3MM paper to blot. The membrane was washed in 6X SSC for 5 minutes at room temperature, and allowed to dry. The DNA was immobilized with UV irradiation exactly as described above. The protocol for the previously described dot blot assay was followed from prehybridization to the last washes, with the volumes of solutions scaled up by a factor of about 1.5. The membrane was incubated for 3.5 hours with 0.4 mL substrate solution ($10^{-3}$ M TOSAP in substrate buffer) before developing with 1.6 mL of $1 \times 10^{-3}$ M Tb:EDTA in 0.4M dimethylamine buffer pH 12.5, as described above. Photographs were taken with the TRP100 camera using the filters described above with an exposure time of 45 seconds.

Figure 13:
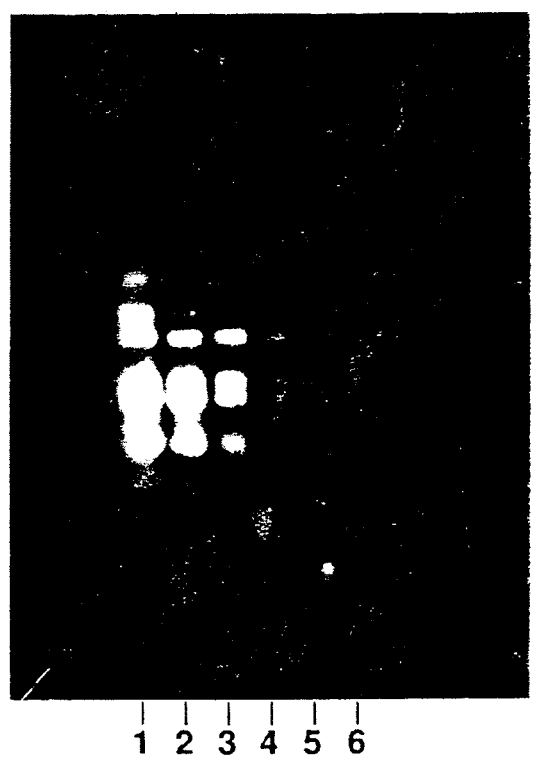
FIG. 13 a time-resolved photograph of digested pBR322 Southern blot hybridization assay, detected using biotinylated pBR322 probe, subsequent binding with avidin-AP, with TOSAP as substrate, and luminescence detection of Tb:TOSA:EDTA complex. Lanes 1 through 6 contain, respectively (from left) 25, 6.2, 1.6, 0.4, 0.1 ng of BstN I digest of pBR322 DNA, 750 ng Hind III digested λ-DNA.

The resulting photograph is illustrated in FIG. 13, showing the presence of higher molecular weight bands from incompletely digested pBR322, and BstN I digested pBR322 bands below (1857, 1060, 929, 383, 121 bases). Samples down to 0.4 ng pBR322 are clearly visible (lanes 1–4), with faint bands from 0.1 ng pBR322 (lane 5). The control λ-DNA (lane 6) does not show any signal, as expected.

Although preferred embodiments of the invention are described herein in detail, it will be understood by those skilled in the art that variations may be made thereto without departing from the spirit of the invention or the scope of the appended claims.

We claim:

1. In a method for detecting luminescence emitted from an excited lanthanide metal chelate associated with an analyte, including the steps of (1) enzymatically converting a selected substrate in a solution by use of an enzyme into a chelator which in the presence of a lanthanide metal ion forms a luminescent lanthanide metal chelate, said substrate in its unconverted form being non-competitive with said lanthanide metal chelate when exposed to radiation which causes said chelate to luminesce and (2) adding said lanthanide metal to said converted substrate to form said lanthanide metal chelate, the improvement comprising:

selecting said substrate from the group of salicyl phosphates represented by the formula (I):

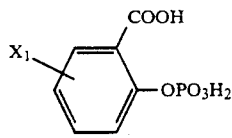

wherein $X_1$ is hydrogen, halogen, $C_1$ to $C_{20}$ alkyl, $C_1$ to $C_{20}$ alkyl containing at least one heteroatom, $C_1$ to $C_{20}$ halogenated alkyl, $C_5$ to $C_{20}$ halogenated aryl, $C_5$ to $C_{20}$ aryl, $C_1$ to $C_{20}$ aryl containing at least one heteroatom, a heteroaromatic group of pyridine, furan, pyrrole, or thiophene which is ring unsubstituted or ring substituted with $C_1$ to $C_{20}$ alkyl or halogen, trityl, 2, 4-difluorophenyl; and $X_1$ is one or more substituents at the 3, 4, 5, or 6 carbon atom of the benzene ring; and increasing the pH of said solution containing said enzymatically converted selected salicyl phosphate of formula (I), to a more alkaline pH in forming said lanthanide metal chelate.

2. A method according to claim 1 wherein $X_1$ is 2, 4-difluorophenyl.

3. In a method of claim 1, said analyte is an enzyme for converting said substrate.

4. In a method of claim 1, said enzyme being conjugated to a biological molecule which is capable of association with said analyte or with a group associated with said analyte.

5. In a method of claim 4, said biological molecule being a nucleic acid probe and said analyte being a complementary nucleic acid sequence to said probe.

6. In a method of claim 5, said nucleic acid probe being a large molecular weight naturally occurring nucleic acid.

7. In a method of claim 5, said nucleic acid being a synthetic oligonucleotide.

8. In a method of claim 5, said luminescence being generated as part of a nucleic acid hybridization assay.

9. In a method of claim 8 wherein said nucleic acid hybridization assay is selected from the group consisting of dot blot hybridization assay, Southern blot or Western blot hybridization assay, sandwich hybridization assay, colony hybridization assay, plaque hybridization assay, in situ hybridization assay and DNA sequencing assay.

10. In a method of claim 4, said biological molecule being an antibody and said analyte being an antigen.

11. In a method of claim 10, said antigen being selected from the group consisting of haptens, proteins, hormones, bacteria, viruses and chemical pharmaceuticals.

12. In a method of claim 1, said lanthanide metal being selected from the group consisting of terbium, europium, samarium and dysprosium.

13. In a method of claim 1, said luminescent detection signal being detected by pulse-excitation time-resolved measurement.

14. In a method of claim 1, said luminescent detection signal being detected by continuous-excitation non-gated measurement.

15. In a method of claim 1, said luminescent detection signal being enhanced upon addition of a co-chelator, polyaminocarboxylic acid.

16. In a method of claim 1, said luminescent detection signal being enhanced upon addition of a co-chelator selected from the group consisting of ethylenediaminetetraacetic acid, diethylenetriaminepentaacetic acid, nitrilotriacetic acid and iminodiacetic acid.

17. In a method of claim 1, said enzyme being alkaline phosphate and said substrate being 5-fluorosalicyl phosphate.

18. In a method of claim 1, said enzyme being alkaline phosphate and said substrate being 5-fluorosalicyl phosphate.

19. In a method of claim 1, said enzyme being alkaline phosphatase and said substrate being 5-tert-octylsalicyl phosphate.

20. In a method of claim 1, said enzyme being alkaline phosphatase and said substrate being 5-(2',4'-difluorophenyl)salicyl phosphate.

21. In a method of claim 1, 18, 19 or 20, said lanthanide metal is terbium and luminescence is detected in the presence of EDTA.

22. In a method of claim 1, said lanthanide metal being terbium.

* * * * *

UNITED STATES PATENT AND TRADEMARK OFFICE
CERTIFICATE OF CORRECTION

PATENT NO. : 5,262,299

DATED : November 16, 1993

INVENTOR(S) : Ramon A. Evangelista, et al.

It is certified that error appears in the above-indentified patent and that said Letters Patent is hereby corrected as shown below:

Column 5, line 31, after "substrate", insert -- . --.

Column 6, line 68, after "lanthanides.", start a new paragraph.

Column 7, line 2, delete "in" (second occurrence) and substitute therefor -- 1:n --.

Column 7, line 28, after "chelate.", start new paragraph.

Column 8, line 27, "Ep" should be -- EP --.

Column 9, line 25, "Plant lectin-Enzyme" should be underlined.

Column 10, line 11, "Hapten-Enzyme" should be underlined.

Column 10, line 46, "Avidin-$\beta$-Glactosidase" should be -- Avidin-$\beta$-Galactosidase --.

Column 10, line 56, "Protein A-Enzyme" should be underlined.

Column 14, line 14, after "results.", start new a paragraph.

Column 19, line 40, "Which" should be -- which --.

UNITED STATES PATENT AND TRADEMARK OFFICE
CERTIFICATE OF CORRECTION

PATENT NO. : 5,262,299

DATED : November 16, 1993

INVENTOR(S) : Ramon A. Evangelista, et al.

It is certified that error appears in the above-indentified patent and that said Letters Patent is hereby corrected as shown below:

Column 21, SCHEME V, "$O_2 + H_2O$" should be on a line between H and OH, and likewise "+ $H_2O_2$ between OH and OH.

Column 23, line 35, "$Er^{3+}$" should be -- $Eu^{3+}$ --.

Column 24, SCHEME VI, line between "N and COO" should be dashed.

Column 24, line 52, "5%" should be -- 15% --.

Column 26, line 10, "Microlite)" should be -- Microlite') --.

Column 27, line 55, "$M^{-1}c^{-1}$" should be -- $M^{-1}cm^{-1}$ --.

Column 29, line 14, "0 38" should be -- 0.38 --.

Column 31, line 57, "Vreland" should be - Vreeland --.

Column 33, line 33, "HRp" should be -- HRP --.

Column 35, line 28, "$^-P$" should be -- $^{31}P$ --.

Column 35, line 31, after "(m, 1H);", insert -- $^{31}P$ --.

Column 36, line 3, "phosphate" should be -- Phosphate --.

UNITED STATES PATENT AND TRADEMARK OFFICE
CERTIFICATE OF CORRECTION

PATENT NO. : 5,262,299

DATED : November 16, 1993

INVENTOR(S) : Ramon A. Evangelista, et al.

It is certified that error appears in the above-indentified patent and that said Letters Patent is hereby corrected as shown below:

Column 37, line 8, "cm" should be -- $cm^{-1}$ --.

Column 39, SCHEME XV, "H" (at the beginning of structural formula) should be -- X --.

Column 40, line 1, "$1 \times 10^{-5}M$" should be -- $1 \times 10^{-3}M$ --.

Column 41, line 58, after "$CDCl_3$", insert -- : --.

Column 43, line 16, "$Eu^3$" should be -- $Eu^{3+}$ --.

Column 43, line 59, after "6", close up space.

Column 44, line 61, "Was" should be -- was --.

Column 46, lines 49-51, after "1," delete remainder of claim 17, and substitute therefor -- $X_1$ is 5-fluoro, 2,4- difluorophenyl, 5-tert-octyl or 5-phenyl. --.

Signed and Sealed this

Twenty-eighth Day of June, 1994

Attest:

BRUCE LEHMAN

*Attesting Officer*    Commissioner of Patents and Trademarks